(12) United States Patent
Tokuhisa

(10) Patent No.: US 9,608,400 B2
(45) Date of Patent: Mar. 28, 2017

(54) LASER DEVICE, AND EXPOSURE DEVICE AND INSPECTION DEVICE PROVIDED WITH LASER DEVICE

(71) Applicant: NIKON CORPORATION, Tokyo (JP)

(72) Inventor: Akira Tokuhisa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 74 days.

(21) Appl. No.: 14/417,986

(22) PCT Filed: Jul. 31, 2013

(86) PCT No.: PCT/JP2013/070717
§ 371 (c)(1),
(2) Date: Jun. 25, 2015

(87) PCT Pub. No.: WO2014/021370
PCT Pub. Date: Feb. 6, 2014

(65) Prior Publication Data
US 2015/0303647 A1    Oct. 22, 2015

(30) Foreign Application Priority Data

Jul. 31, 2012  (JP) .................................. 2012-169643
Jul. 31, 2012  (JP) .................................. 2012-169644

(51) Int. Cl.
*G03B 27/54*        (2006.01)
*G03B 27/74*        (2006.01)
(Continued)

(52) U.S. Cl.
CPC ........... *H01S 3/2391* (2013.01); *G01N 21/88* (2013.01); *G03F 7/70058* (2013.01);
(Continued)

(58) Field of Classification Search
CPC ....... G03F 7/70058; G01N 2201/06113; H01S 3/2391
(Continued)

(56) References Cited

U.S. PATENT DOCUMENTS

2003/0174393 A1*  9/2003  Maeda .................... B82Y 20/00
                                                  359/344
2004/0012844 A1*  1/2004  Ohtsuki ............. B23K 26/0643
                                                  359/341.1
(Continued)

FOREIGN PATENT DOCUMENTS

JP        H11-52443 A       2/1999
JP     2000-171843 A        6/2000
(Continued)

OTHER PUBLICATIONS

Nov. 5, 2013 International Search Report issued in International Application No. PCT/JP2013/070717.

*Primary Examiner* — Hung Henry Nguyen
(74) *Attorney, Agent, or Firm* — Oliff PLC

(57) ABSTRACT

A laser device, includes: a laser light generating unit generates laser lights with first and second wavelengths; an amplifying unit amplifies the lights with first and second wavelengths the first and the second amplified lights; a wavelength converting unit that generates a light output, either of first converted light wavelength conversion of the first amplified light and the second amplified light, or of the first converted light and the second converted light wavelength conversion of the second amplified light; and a control unit that controls operation of the laser light generating unit, wherein: the control unit controls an output condition of the light output by adjusting a temporal overlap, of the first converted light and the second amplified light, or the first and second converted lights, through control of
(Continued)

Figure 1:
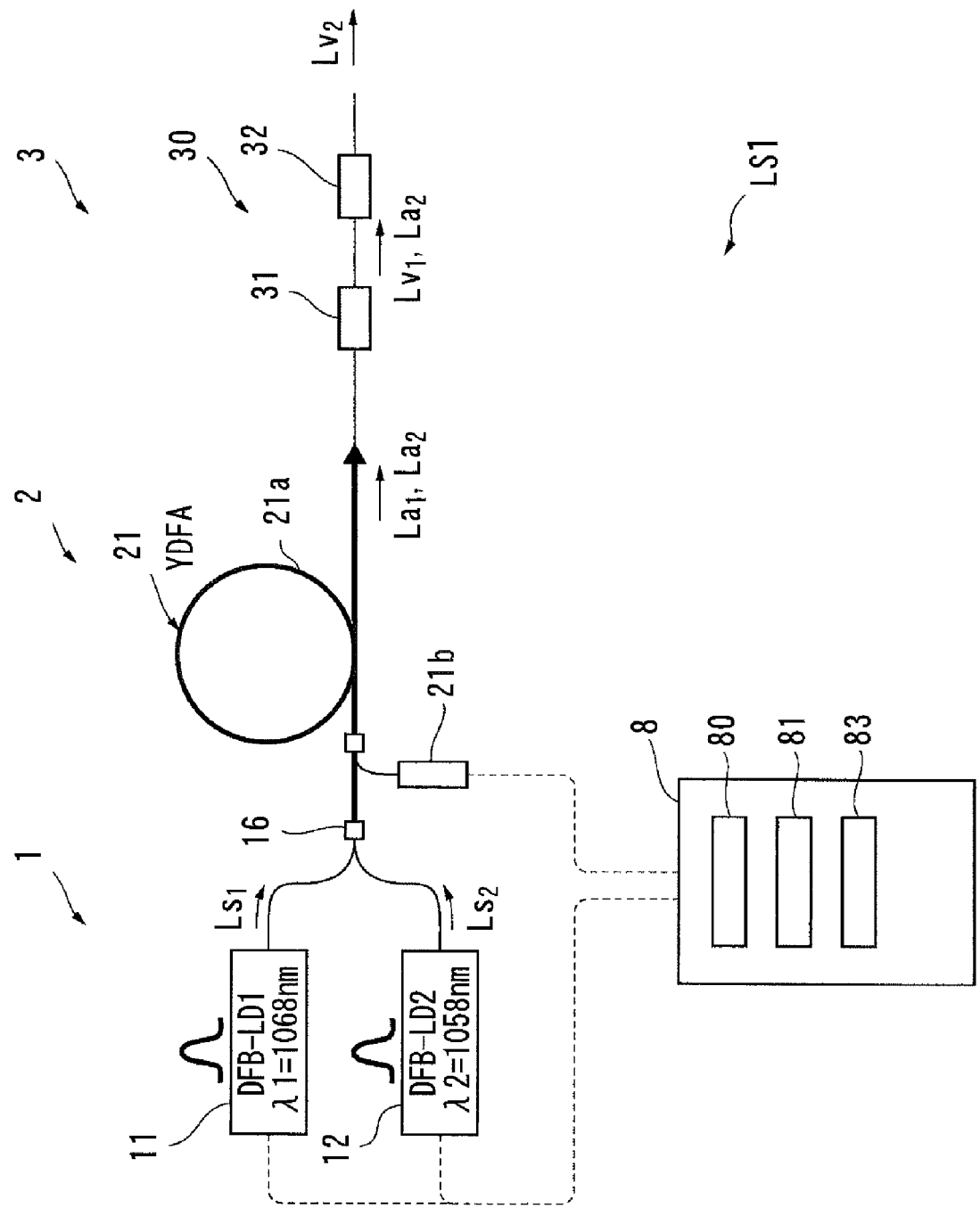

relative timings of the laser light with the first and second wavelengths.

15 Claims, 14 Drawing Sheets

(51) Int. Cl.
  *H01S 3/23* (2006.01)
  *H01S 5/00* (2006.01)
  *H01S 5/0683* (2006.01)
  *G01N 21/88* (2006.01)
  *G03F 7/20* (2006.01)
  *H01S 3/067* (2006.01)
  *H01S 3/16* (2006.01)
  *H01S 5/062* (2006.01)
  *H01S 5/40* (2006.01)

(52) U.S. Cl.
  CPC .......... *H01S 5/0092* (2013.01); *H01S 5/0683* (2013.01); *G01N 2201/06113* (2013.01); *H01S 3/06754* (2013.01); *H01S 3/1618* (2013.01); *H01S 5/06216* (2013.01); *H01S 5/06246* (2013.01); *H01S 5/4087* (2013.01)

(58) Field of Classification Search
  USPC .................. 355/67–71; 372/20; 359/344
  See application file for complete search history.

(56) References Cited

U.S. PATENT DOCUMENTS

| | | |
|---|---|---|
| 2006/0078012 A1 | 4/2006 | Miwa |
| 2009/0110012 A1 | 4/2009 | Tokuhisa et al. |
| 2010/0225897 A1 | 9/2010 | Fermann et al. |
| 2011/0268142 A1 | 11/2011 | Tokuhisa et al. |
| 2012/0081694 A1 | 4/2012 | Fermann et al. |
| 2012/0145902 A1 | 6/2012 | Fermann et al. |
| 2013/0044772 A1* | 2/2013 | Ensher ................ H01S 5/4087 372/20 |
| 2013/0148128 A1 | 6/2013 | Fermann et al. |

FOREIGN PATENT DOCUMENTS

| | | |
|---|---|---|
| JP | 2004-086193 A | 3/2004 |
| JP | 2007-206452 A | 8/2007 |
| JP | 2011-158749 A | 8/2011 |
| JP | 2012-002965 A | 1/2012 |
| WO | 2004/086121 A1 | 10/2004 |
| WO | 2007/055110 A1 | 5/2007 |
| WO | 2010/101690 A1 | 9/2010 |

* cited by examiner

LASER DEVICE, AND EXPOSURE DEVICE AND INSPECTION DEVICE PROVIDED WITH LASER DEVICE

TECHNICAL FIELD

The present invention relates to a laser device comprising a laser light generating unit that generates laser light, an amplifying unit that amplifies the laser light and a wavelength converting unit that converts the wavelength of the amplified laser light. It further relates to a laser system such as an exposure device or an inspection device provided with the laser device.

BACKGROUND ART

A laser device such as that described above is used as a light source in a laser system that may be, for instance, a microscope, a profile measurement device, an exposure device or an inspection device. The output wavelength of the laser device is set in correspondence to the purpose of use and functions of the system in which the laser device is installed. Laser devices in the known art include those capable of outputting deep ultraviolet light with a wavelength of 193 nm and those capable of outputting ultraviolet light with a wavelength of 355 nm. The wavelength of the laser light generated by the laser light generating unit, a specific number of rows and a specific number of stages over which amplifiers are disposed in the amplifying unit, and types of, and a specific combination of wavelength conversion optical elements included in the wavelength converting unit are all set in correspondence to the purpose of use, functions and the like (see patent literature 1).

Several methods through which light output can be turned ON/OFF at high speed in this type of laser device have been proposed. In a first art, for instance, a wavelength conversion optical system is configured with a plurality of parallel light paths (e.g., a first system and a second system) and a serial light path at which light outputs emitted from these parallel light paths enter in a superimposed state, with a light source and an amplifier disposed in correspondence to each parallel light path. Pulse light emitted from the light source and amplified by the amplifier is input to the corresponding light path, i.e., the first system and the second system, and the timing with which light is emitted at each light source is adjusted. Namely, the temporal overlap of the pulse light having passed through the first system and the pulse light having passed through the second system, which occurs at the wavelength conversion optical element disposed at the last stage in the serial path, is controlled, and through this control, ON/OFF control of the light output is achieved (see patent literature 2).

In a second art, a wavelength conversion optical system, constituted with a single serial light path configured with a plurality of wavelength conversion optical elements, includes a single set of a light source and an amplifier. Seed light emitted from the light source is switched to a high peak power state or to a low peak power state, and ON/OFF control of the light output is achieved by varying the wavelength conversion efficiency through this switchover.

CITATION LIST

Patent Literature

Patent literature 1: Japanese Laid-Open Patent Publication No. 2004-86193
Patent literature 2: International Publication 2007/055110

SUMMARY OF THE INVENTION

Technical Problem

In the first art, light is input at all times at the individual light sources, the individual amplifiers and most of the wavelength conversion optical elements constituting the laser device, thereby assuring thermal stability, which enables high speed and stable ON/OFF control of the light output. However, the first art cannot be adopted in conjunction with a simple structure through which light output with a wavelength of 355 nm is generated through a third harmonic from a single light source. In order to allow the first art to be adopted in such a simple structure, a plurality of light sources and a plurality of amplifiers, in quantities corresponding to the number of parallel circuits forming the wavelength conversion optical system, will be required, which is bound to complicate the structure of the laser device.

While the second art allows the laser device to assume a simple structure, the power of the laser light entering the wavelength conversion optical elements fluctuates as the light output is turned ON/OFF, resulting in significant changes in the thermal conditions at the wavelength conversion optical elements. For this reason, the second art is yet to overcome the challenge of high speed and stable ON/OFF control of the light output.

An object of the present invention, having been completed by addressing the problems discussed above, is to provide a laser device capable of controlling the light output at high speed while assuring stability through a simple structure. Another object of the present invention is to provide an exposure device, an inspection device and the like each achieving a simple overall system structure.

Solution to Problems

According to the first aspect of the present invention, a laser device, comprises: a laser light generating unit that includes a first light source that generates pulse laser light with a first wavelength and a second light source that generates pulse laser light with a second wavelength; an amplifying unit equipped with an amplifier achieving gain in light in a wavelength range that includes the first wavelength and the second wavelength, which outputs first amplified light obtained by amplifying the laser light with the first wavelength and second amplified light obtained by amplifying the laser light with the second wavelength; a wavelength converting unit that includes a wavelength conversion optical element, which either converts the first amplified light to first converted light through wavelength conversion and generates a light output through wavelength conversion of the first converted light and the second amplified light, or converts the first amplified light to first converted light and the second amplified light to second converted light and generates a light output through wavelength conversion of the first converted light and the second converted light; and a control unit that controls operation of the laser light generating unit, wherein: the control unit controls an output condition of the light output by adjusting a temporal overlap of the first converted light and the second amplified light or a temporal overlap of the first converted light and the second converted light at a position at which the light output is generated in the wavelength converting unit, through control of timing with which the laser light with the first wavelength is output from the first light source and the timing with which the laser light with the second wavelength is output from the second light source relative to each other.

According to the second aspect of the present invention, in the laser device according to the first aspect, it is preferred that the wavelength converting unit includes a first wavelength conversion optical element that converts the first amplified light to first converted light through wavelength conversion and allows the second amplified light to be transmitted and a second wavelength conversion optical element that generates second converted light through wavelength conversion of the second amplified light transmitted through the first wavelength conversion optical element and the first converted light; and the control unit controls an output condition of the second converted light by adjusting a temporal overlap of the first converted light and the second amplified light at the second wavelength conversion optical element through control of the timing with which the laser light with the first wavelength is output from the first light source and the timing with which the laser light with the second wavelength is output from the second light source relative to each other.

According to the third aspect of the present invention, in the laser device according to the second aspect, it is preferred that the first wavelength and the second wavelength are individually set to such values that a phase matching condition for generating a sum frequency of the first converted light and the second amplified light is satisfied and a phase matching condition for generating a sum frequency of the first converted light and the first amplified light is not satisfied at the second wavelength conversion optical element.

According to the fourth aspect of the present invention, in the laser device according to the second aspect or third aspect, it is preferred that the first wavelength and the second wavelength are individually set to such values that a phase matching condition for generating a harmonic of the first amplified light is satisfied and a phase matching condition for generating a harmonic of the second amplified light is not satisfied at the first wavelength conversion optical element.

According to the fifth aspect of the present invention, in the laser device according to any one of the second through fourth aspects, it is preferred that the control unit controls ON/OFF of the second converted light provided as the light output by switching between a condition in which the first converted light and the second amplified light temporally overlap and a condition in which the first converted light and the second amplified light do not temporally overlap at the second wavelength conversion optical element.

According to the sixth aspect of the present invention, in the laser device according to any one of the second through fifth aspects, it is preferred that the control unit controls power of the second converted light provided as the light output by altering the extent to which the first converted light and the second amplified light temporally overlap at the second wavelength conversion optical element.

According to the seventh aspect of the present invention, in the laser device according to the first aspect, it is preferred that the wavelength converting unit includes a first wavelength conversion optical element that converts the first amplified light to first converted light through wavelength conversion and allows the second amplified light to be transmitted, a second wavelength conversion optical element that converts the second amplified light having been transmitted through the first wavelength conversion optical element to second converted light through wavelength conversion and allows the first converted light to be transmitted, and a third wavelength conversion optical element that generates third converted light through wavelength conversion of the first converted light and the second converted light; and the control unit controls an output condition of the third converted light by adjusting a temporal overlap of the first converted light and the second converted light at the third wavelength conversion optical element through control of the timing with which the laser light with the first wavelength is output from the first light source and the timing with which the laser light with the second wavelength is output from the second light source relative to each other.

According to the eighth aspect of the present invention, in the laser device according to the seventh aspect, it is preferred that the first wavelength and the second wavelength are individually set to such values that a phase matching condition for generating a sum frequency of the first converted light and the second converted light is satisfied and any of phase matching conditions for generating sum frequencies and second harmonics other than the sum frequency is not satisfied at the third wavelength conversion optical element.

According to the ninth aspect of the present invention, in the laser device according to the seventh aspect or eighth aspect, it is preferred that the first wavelength and the second wavelength are individually set to such values that a phase matching condition for generating a harmonic of the first amplified light is satisfied and a phase matching condition for generating a harmonic of the second amplified light is not satisfied at the first wavelength conversion optical element and that a phase matching condition for generating a harmonic of the second amplified light is satisfied and a phase matching condition for generating a harmonic of the first amplified light is not satisfied at the second wavelength conversion optical element.

According to the tenth aspect of the present invention, in the laser device according to any one of the seventh through ninth aspects, it is preferred that the control unit controls ON/OFF of the third converted light provided as the light output by switching between a condition in which the first converted light and the second converted light temporally overlap and a condition in which the first converted light and the second amplified light do not temporally overlap at the third wavelength conversion optical element.

According to the eleventh aspect of the present invention, in the laser device according to any one of the seventh through tenth aspects, it is preferred that the control unit controls power of the third converted light provided as the light output by altering the extent to which the first converted light and the second converted light temporally overlap at the third wavelength conversion optical element.

According to the twelfth aspect of the present invention, an exposure device, comprises: a laser device according to any one of the first 1 through eleventh aspects; a mask supporting unit that holds a photomask having a predetermined exposure pattern formed thereat; an exposure target object supporting unit that holds an exposure target object; an illumination optical system that illuminates the photomask held at the mask supporting unit with laser light output from the laser device; and a projection optical system that projects light having been transmitted through the photomask onto the exposure target object held at the exposure target object supporting unit.

According to the thirteenth aspect of the present invention, an inspection device, comprises: a laser device according to any one of the first 1 through eleventh aspects; an illumination optical system that illuminates the inspection target object held at the inspection target object supporting unit with laser light output from the laser device; and a projection optical system that projects light departing the inspection target object toward a detector.

Advantageous Effect of the Invention

The amplifying unit in the laser device according to the present invention comprises an amplifier that achieves gain in light within a wavelength range that includes a first wavelength and a second wavelength, and laser light with the first wavelength and laser light with the second wavelength, output from the laser light generating unit, are amplified by common amplifier. The control unit adjusts the temporal overlap of the first converted light and the second amplified light at the wavelength converting unit by controlling the timing with which the laser light with the first wavelength is output and the timing with which the laser light with the second wavelength is output relative to each other so as to ultimately control the output condition of the light output. In the laser device according to the present invention, which is configured with a single light path achieved by connecting an amplifier and a wavelength conversion optical system in series, the first light source, the second light source, the amplifier and the wavelength conversion optical elements remain thermally stable. As a result, high speed and stable ON/OFF control of the light output is achieved through adjustment of the operation timing of the first light source and the second light source executed by the control unit. In other words, a laser device that enables high speed and stable ON/OFF control of the light output through a simple structure can be provided.

The exposure device according to the present invention includes the laser device achieved in the first aspect. Thus, the exposure device can be provided as a system assuming a simple overall configuration.

The inspection device according to the present invention includes the laser device achieved in the first aspect. Thus, the inspection device can be provided as a system assuming a simple overall configuration.

BRIEF DESCRIPTION OF THE DRAWINGS (FIG. 1) A schematic diagram showing the structure of the laser device achieved in a first embodiment, representing an application example of the present invention (FIG. 2) An illustration of the pulse conditions manifesting in the wavelength converting unit when the light output is ON in the laser device achieved in the first embodiment (FIG. 3) An illustration of the pulse conditions with regard to the first converted light and the second amplified light, manifesting at the second wavelength conversion optical element when the light output is ON in the laser device achieved in the first embodiment (FIG. 4) An illustration of the pulse conditions manifesting in the wavelength converting unit when the light output is OFF in the laser device achieved in the first embodiment (FIG. 5) An illustration of the pulse conditions with regard to the first converted light and the second amplified light, manifesting at the second wavelength conversion optical element when the light output is OFF in the laser device achieved in the first embodiment (FIG. 6) An illustration of the pulse train of the first converted light and the pulse train of the second amplified light overlapping at various overlap rates at the second wavelength conversion optical element in the laser device achieved in the first embodiment (FIG. 7) A schematic diagram showing the structure of the laser device achieved in a second embodiment, representing an application example of the present invention (FIG. 8) An illustration of the pulse conditions manifesting in the wavelength converting unit when the light output is ON in the laser device achieved in the second embodiment (FIG. 9) An illustration of the pulse conditions with regard to the first converted light and the second converted light, manifesting at the second wavelength conversion optical element when the light output is ON in the laser device achieved in the second embodiment (FIG. 10) An illustration of the pulse conditions manifesting in the wavelength converting unit when the light output is OFF in the laser device achieved in the second embodiment (FIG. 11) An illustration of the pulse conditions with regard to the first converted light and the second converted light, manifesting at the third wavelength conversion optical element when the light output is OFF in the laser device achieved in the second embodiment (FIG. 12) An illustration of the pulse train of the first converted light and the pulse train of the second converted light overlapping at various overlap rates at the third wavelength conversion optical element in the laser device achieved in the second embodiment (FIG. 13) A schematic diagram showing the structure of an exposure device representing a first application example for a system equipped with the laser device according to the present invention (FIG. 14) A schematic diagram showing the structure of an inspection device representing a second application example for a system equipped with the laser device according to the present invention

DESCRIPTION OF EMBODIMENTS

The following is a description of the embodiments of the present invention, given in reference to drawings. FIG. 1 provides a schematic diagram showing the structure of a laser device LS1 achieved as the first embodiment of the present invention. The laser device LS1 comprises a laser light generating unit 1 that generates pulse laser light (seed light), an amplifying unit 2 that amplifies the seed light generated by the laser light generating unit 1, a wavelength converting unit 3 that converts the wavelength of amplified light output from the amplifying unit 2, and a control unit 8 that controls operations of these units.

Numerous structural embodiments are conceivable for the specific structures that may be adopted for the laser light generating unit 1, the amplifying unit 2, and the wavelength converting unit 3. The first embodiment will be described in reference to an example in which the seed light generated by the laser light generating unit 1 is infrared light with a wavelength around 1.06 μm and the light output by the wavelength converting unit 3 is ultraviolet light with a wavelength of 355 nm.

The laser light generating unit 1 includes two light sources with oscillation wavelengths thereof slightly different from each other. Namely, the laser light generating unit 1 includes a first light source 11 that generates seed light with a first wavelength $\lambda_1$ and a second light source 12 that generates seed light with a second wavelength $\lambda_2$. A wavelength difference $\Delta\lambda$ between the first wavelength $\lambda_1$ and the second wavelength $\lambda_2$ is 10 nm, the first wavelength $\lambda_1$ is equal to 1068 nm and the second wavelength $\lambda_2$ is equal to 1058 nm.

The first light source 11 and the second light source 12 are each constituted with a DFB (distributed feedback) semiconductor laser. The oscillation wavelength of the DFB semiconductor laser can be set to a desired value within a predetermined range by controlling the operating temperature thereof via a temperature adjuster. CW oscillation and pulse oscillation can be induced at the DFB semiconductor laser through waveform control of its drive current. In the laser device LS1 in the first embodiment, repetitive pulse oscillation is induced at a predetermined frequency selected from a frequency range of for instance, approximately 1 to 10 MHz at the first light source 11 and the second light source 12. The operations of the first light source 11 and the second light source 12 are controlled by the control unit 8. Pulse seed light $Ls_1$ with the first wavelength $\lambda_1$ and pulse seed light $Ls_2$ with the second wavelength $\lambda_2$ output from the laser light generating unit 1 are multiplexed by a coupler 16 and thus enter the amplifying unit 2 in a multiplexed state.

The amplifying unit 2 assumes a structure that includes a fiber amplifier 21 that amplifies the seed light output from the laser light generating unit 1. The fiber amplifier 21 achieves gain in light within a wavelength range that includes the first wavelength $\lambda_1$ and the second wavelength $\lambda_2$. An ytterbium doped fiber amplifier (YDFA) is preferably used as this fiber amplifier.

An ytterbium doped fiber amplifier (YDFA) 21 is constituted with, as primary components thereof, an amplification fiber 21a having ytterbium (Yb) doped in a core thereof and an excitation light source 21b that provides excitation light to the amplification fiber. The gain of the fiber amplifier 21 is controlled by adjusting the power of the excitation light that excites the amplification fiber 21a, and more specifically, by adjusting, via the control unit 8, the drive power of the excitation light source 21b.

The YDFA 21, achieving gain in the wavelength range of 1000 to 1100 nm, amplifies both the seed light $Ls_1$ with the first wavelength $\lambda_1$ of 1068 nm and the seed light $Ls_2$ with the second wavelength $\lambda_2$ of 1058 nm. While the seed light $Ls_1$ with the first wavelength $\lambda_1$ and the seed light $Ls_2$ with the second wavelength $\lambda_2$ are multiplexed via the coupler 16 and thus enter the fiber amplifier 21 in a multiplexed state, they are amplified independently of each other due to the wavelength difference $\Delta\lambda$ of approximately 10 nm between the first wavelength $\lambda_1$ and the second wavelength $\lambda_2$. Thus, first amplified light $La_1$ resulting from amplification of the seed light $Ls_1$ with the first wavelength and second amplified light $La_2$ resulting from amplification of the seed light $Ls_2$ with the second wavelength are output from the fiber amplifier 21 (amplifying unit 2). The first amplified light $La_1$ and the second amplified light $La_2$ output from the amplifier unit 2 enter the wavelength converting unit 3.

While the amplifying unit 2 in the description provided above includes the fiber amplifier 21 disposed at a single stage for purposes of simplification, the amplifying unit 2 may instead be configured with a plurality of fiber amplifiers connected in series by, for instance, connecting in series a plurality of single clad fiber amplifiers or by connecting in series a single clad fiber amplifier and a double clad fiber amplifier.

The wavelength converting unit 3 includes a wavelength conversion optical system 30, through which the first amplified light $La_1$ and the second amplified light $La_2$, output from the amplifying unit 2, propagates. The wavelength conversion optical system 30, constituted with a first wavelength conversion optical element 31 and a second wavelength conversion optical element 32 as primary components thereof, includes a lens, a waveplate and the like (not shown). The first amplified light $La_1$ and the second amplified light $La_2$, having entered the wavelength converting unit 3, are condensed via the lens and thus enters the first wavelength conversion optical element 31 in a condensed state.

The first wavelength conversion optical element 31, constituted of a nonlinear optical crystal, generates a second harmonic (first converted light $Lv_1$) with a wavelength that is ½ of the wavelength $\lambda_1$ of the first amplified light $La_1$ through second harmonic generation (SHG). However, the second amplified light $La_2$ with the wavelength $\lambda_2$ is allowed to be transmitted through the first wavelength conversion optical element 31 without undergoing wavelength conversion. In other words, due to the wavelength difference $\Delta\lambda$ between the first amplified light $La_1$ and the second amplified light $La_2$, a phase matching condition for second harmonic generation is satisfied for the first amplified light $La_1$ and a phase matching condition for generating a second harmonic of the second amplified light $La_2$ is not satisfied at the first wavelength conversion optical element 31 in the laser device achieved in the first embodiment.

An LBO ($LiB_3O_5$) crystal is used as the first wavelength conversion optical element 31, in noncritical phase matching (NCPM) state, which generates a second harmonic of the first amplified light $La_1$. No walkoff occurs with regard to the first converted light $Lv_1$ with the a wavelength of 534 nm generated as the second harmonic of the first amplified light $La_1$, as long as the noncritical phase matching state is sustained. For this reason, efficient wavelength conversion is enabled by assuring a sufficient interaction length at the first wavelength conversion optical element 31. In addition, since the beam section of the first converted light output therefrom has not become ellipsoid, it is not necessary to dispose a beam-shaping optical element such as a cylindrical lens between the first wavelength conversion optical element 31 and the second wavelength conversion optical element 32 and thus, no loss occurs in the amount of light entering the second wavelength conversion optical element 32.

The use of an LBO crystal to constitute the first wavelength conversion optical element 31 will be described in specific detail. For instance, an LBO crystal assuming a length of approximately 20 mm measured along the optical axis may be used. At such a wavelength conversion optical element, the acceptance wavelength range to satisfy the phase matching condition is approximately several nm for harmonic generation of light having a wavelength substantially equal to the first wavelength $\lambda_1$ at predetermined temperature. Thus, if the temperature of the crystal constituting the first wavelength conversion optical element 31 is set so as to satisfy the phase matching condition for the first amplified light $La_1$ with the 1068 nm wavelength, it can be ensured that the phase matching condition for second harmonic generation will be satisfied only with regard to the first amplified light $La_1$ without satisfying the phase matching condition with respect to the second amplified light $La_2$ having a wavelength different from that of the first amplified light $La_1$ by 10 nm. As a result, at the first wavelength conversion optical element 31, the first amplified light $La_1$ alone undergoes wavelength conversion to result in the generation of a second harmonic, i.e., the first converted light $Lv_1$, but the second amplified light $La_2$ is transmitted through the first wavelength conversion optical element 31 without undergoing wavelength conversion.

While the first wavelength conversion optical element 31 is constituted with an LBO crystal in the noncritical phase matching (NCPM) state in the example described above, a similar effect attributable to the wavelength difference $\Delta\lambda$ can be induced at a first wavelength conversion optical element constituted of a nonlinear optical crystal, such as an LBO crystal or a BBO (β-BaB$_2$O$_4$), assuming a critical phase matching (CPM) state. Namely, by setting the angular position of the first wavelength conversion optical element 31 so as to satisfy the phase matching condition for second harmonic generation with regard to the first amplified light La$_1$, it can be ensured that the first amplified light La$_1$ alone undergoes wavelength conversion to result in generation of first converted light Lv$_1$ while allowing the second amplified light La$_2$ to be transmitted without undergoing wavelength conversion. A similar effect can be induced in conjunction with a quasi-phase matching (QPM) crystal such as a PPLN (Periodically Poled LiNbO$_3$) crystal or a PPLT (Periodically Poled LiTaO$_3$) crystal.

Once the first amplified light La$_1$ and the second amplified light La$_2$ enter the first wavelength conversion optical element 31, the first amplified light La$_1$ with the 1068 nm wavelength alone undergoes wavelength conversion to result in generation of the first converted light Lv$_1$ with the wavelength of 534 nm and the second amplified light La$_2$ with the 1058 nm wavelength is transmitted through without undergoing wavelength conversion. The plane of polarization of either the first converted light Lv$_1$ with the 534 nm wavelength having been generated as the second harmonic of the first amplified light La$_1$ at the first wavelength conversion optical element 31 or the second amplified light La$_2$ with the 1058 nm wavelength having been transmitted through the first wavelength conversion optical element 31, (e.g., the second amplified light), is rotated by 90° via a dual wavelength waveplate, and the first converted light Lv$_1$ and the second amplified light La$_2$ then enter the second wavelength conversion optical element 32 in a condensed state (the explanation is given in reference to this example by assuming that the first amplified light La$_1$ and the second amplified light La$_2$, as they are emitted from the fiber amplifier 21, are polarized along an identical direction).

The second wavelength conversion optical element 32, constituted of a nonlinear optical crystal, generates a sum frequency of the first converted light Lv$_1$ and the second amplified light La$_2$ through sum frequency generation (SFG). The light entering the second wavelength conversion optical element 32 includes the component attributable to the first amplified light La$_1$ having been transmitted through the first wavelength conversion optical element 31 without undergoing wavelength conversion. However, while a phase matching condition that allows generation of a sum frequency of the first converted light Lv$_1$ with the 534 nm wavelength and the second amplified light La$_2$ with the 1058 nm wavelength is satisfied at the second wavelength conversion optical element 32, the second wavelength conversion optical element 32 does not assure a phase matching condition for generating a sum frequency with the first amplified light La$_1$ with a wavelength greater than that of the second amplified light La$_2$ by 10 nm and the first converted light Lv$_1$ with the 534 nm wavelength. This means that the sum frequency of the first amplified light La$_1$ and the first converted light Lv$_1$ with the 534 nm wavelength is not generated.

An LBO crystal may be used as the second wavelength conversion optical element 32, in type I critical phase matching (CPM) state, that generates the sum frequency of the first converted light Lv$_1$ and the second amplified light La$_2$. The crystal constituting the second wavelength conversion optical element 32 is cut out so as to assure a phase matching condition for generating second converted light Lv$_2$ with a wavelength of 355 nm through sum frequency generation of the first converted light Lv$_1$ with the 534 nm wavelength and the second amplified light La$_2$ with the 1058 nm wavelength. In more specific terms, the second wavelength conversion optical element 32 is constituted of an LBO crystal assuming a length of approximately 20 mm measured along the optical axis, which is cut out by adjusting the angular position of the incoming light relative to the crystal. At such a second wavelength conversion optical element, the phase matching condition for sum frequency generation is satisfied with regard to the first converted light Lv$_1$ and the second amplified light La$_2$ to result in the generation of the second converted light Lv$_2$ with the 355 nm wavelength but no sum frequency is generated in conjunction with the first converted light Lv$_1$ and the first amplified light La$_1$, since the phase matching condition for sum frequency generation is not satisfied with regard to the first converted light Lv$_1$ and the first amplified light La$_1$.

It is to be noted that the second wavelength conversion optical element 32 used for purposes of second converted light generation may instead be constituted of a BBO (β-BaB$_2$O$_4$) crystal or a CLBO (CsLiB$_6$O$_{10}$) crystal. The second converted light Lv$_2$ with the 355 nm wavelength generated at the second wavelength conversion optical element 32 is emitted from the wavelength converting unit 3 and is ultimately output from the laser device LS1.

In the laser device LS1, high speed and stable control of the light output, i.e., the second converted light Lv$_2$ is enabled through control of the operation of the laser light generating unit 1 executed by the control unit 8. As has already been described, the first light source 11, which generates the seed light Ls$_1$ with the first wavelength $\lambda_1$ and the second light source 12, which generates the seed light Ls$_2$ with the second wavelength $\lambda_2$, are disposed in the laser light generating unit 1. In the first embodiment, the control unit 8 controls the operations of the first light source and the second light source so as to achieve high speed and stable control of the light output.

The control unit 8 is configured so as to include a clock generator 80 that generates a clock signal with a frequency of approximately 100 MHz, to be used for reference in control of the operations of the various units, a light source driver 81 and a light source controller 83. The light source driver 81 generates a first drive signal used to drive the first light source 11 and a second drive signal used to drive the second light source 12 in reference to the clock signal generated by the clock generator 80. The light source controller 83 outputs a command signal to the light source driver 81 based upon an output command input thereto through a processing program in the system in which the laser device LS1 is installed or via an operation panel.

The first drive signal used to drive the first light source 11 and the second drive signal used to drive the second light source 12 in the laser device LS1 achieved in the first embodiment are each generated as a pulse train formed with pulses with a ON time of 1 to several nsec occurring with a pulse repetition frequency of approximately 1 to 10 MHz. The following description will be given by assuming that the first drive signal and the second drive signal are each generated as a pulse train with a 1 nsec ON time and a 1 MHz repetition frequency.

Figure 2:
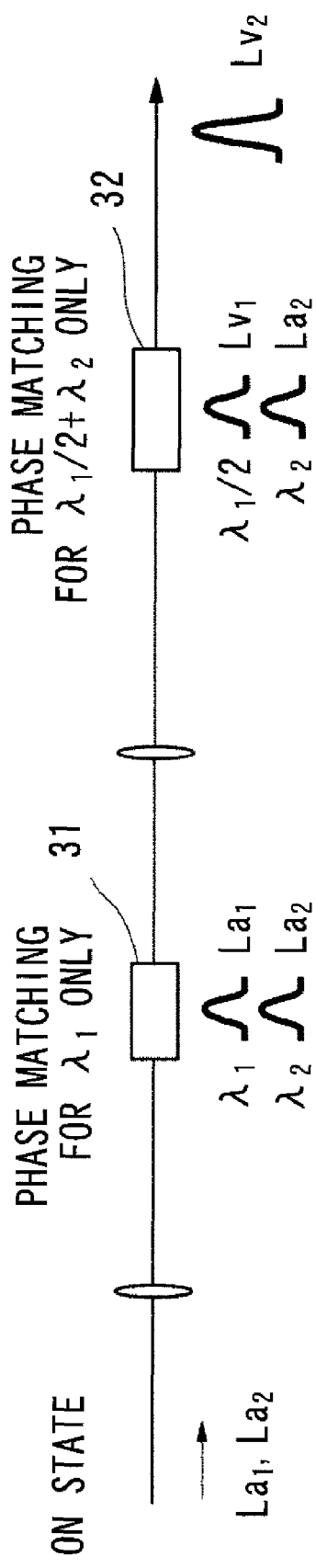
Figure 3:
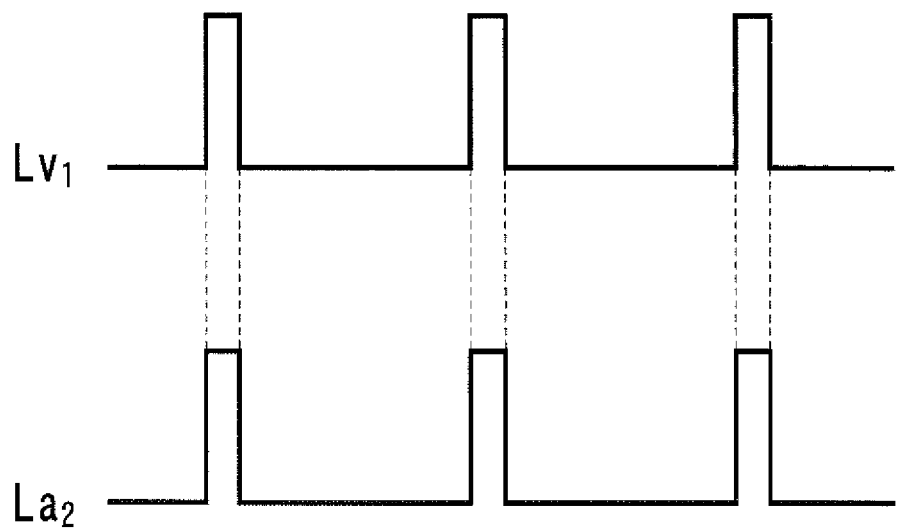

If the output command input to the control unit 8 via an operation panel or the like is an ON command for outputting the second converted light (hereafter referred to as a "light output") Lv$_2$ with the 355 nm wavelength, the light source controller 83 outputs an output ON command signal to the light source driver 81. Under these circumstances, the light source driver 81 controls the output timing with which the seed light $Ls_1$ with the first wavelength is emitted from the first light source 11 and the output timing with which the seed light $Ls_2$ with the second wavelength is emitted from the second light source 12 relative to each other so as to achieve a temporal overlap of a pulse train of the first converted light $Lv_1$ and a pulse train of the second amplified light $La_2$ at the second wavelength conversion optical element 32, as indicated in FIG. 2 and FIG. 3.

In more specific terms, the light source driver 81 generates the first drive signal and the second drive signal with specific timing (identical timing if the first converted light $Lv_1$ and the second amplified light $La_2$ assume a matching optical path length) so that the pulse train of the first converted light $Lv_1$ and the pulse train of the second amplified light $La_2$ temporally overlap each other at the second wavelength conversion optical element 32.

The seed light $Ls_1$ with the first wavelength emitted from the first light source 11 and the seed light $Ls_2$ with the second wavelength emitted from the second light source 12 are individually amplified by the fiber amplifier 21 and thus respectively become the first amplified light $La_1$ and the second amplified light $La_2$, which then enter the first wavelength conversion optical element 31 in a condensed state. At the first wavelength conversion optical element 31, the first amplified light $La_1$ alone undergoes wavelength conversion to result in generation of the first converted light $Lv_1$ while the second amplified light $La_2$ with a wavelength manifesting the wavelength difference $\Delta\lambda$ relative to the first wavelength $\lambda_1$ is transmitted without undergoing wavelength conversion. The first converted light $Lv_1$ generated at the first wavelength conversion optical element 31, the second amplified light $La_2$ transmitted through the first wavelength conversion optical element 31 and the component of the first amplified light $La_1$ that is transmitted through the first wavelength conversion optical element 31 without undergoing wavelength conversion all enter the second wavelength conversion optical element 32 in a condensed state.

Settings are selected for the second wavelength conversion optical element 32 so that the pulse trains of the first converted light $Lv_1$ and the second amplified light $La_2$ having entered therein temporally overlap each other. In addition, the second wavelength conversion optical element 32 is set so that the phase matching condition for generating the sum frequency of the first converted light $Lv_1$ and the second amplified light $La_2$ alone is satisfied without satisfying the phase matching condition for generating the sum frequency of the first converted light $Lv_1$ and the first amplified light $La_1$. As a result, light output (second converted light) $Lv_2$ with the 355 nm wavelength is generated at the second wavelength conversion optical element 32 through the sum frequency generation of the first converted light $Lv_1$ and the second amplified light $La_2$ and this light is ultimately output from the laser device LS1.

Figure 4:
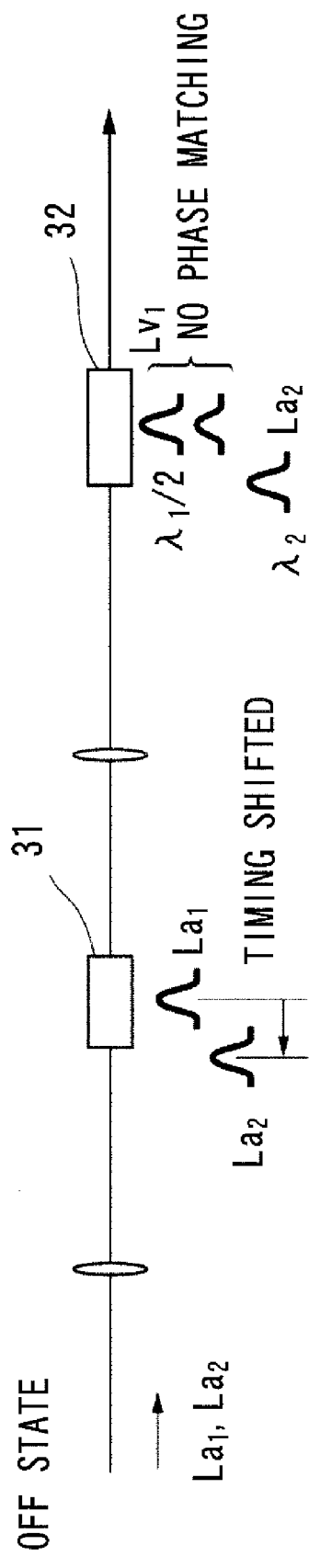
Figure 5:
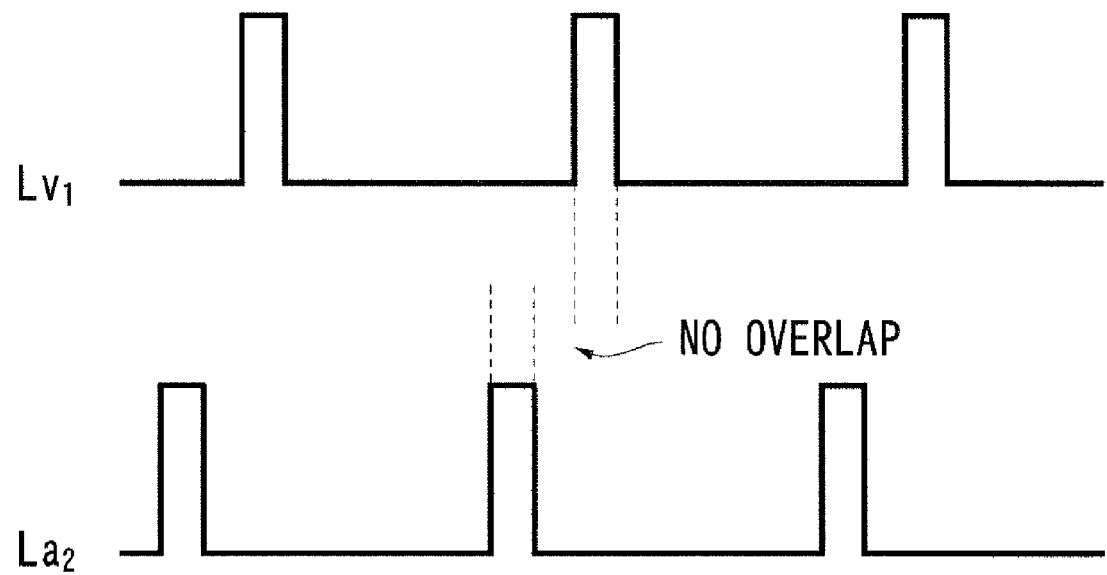
Figure 6:
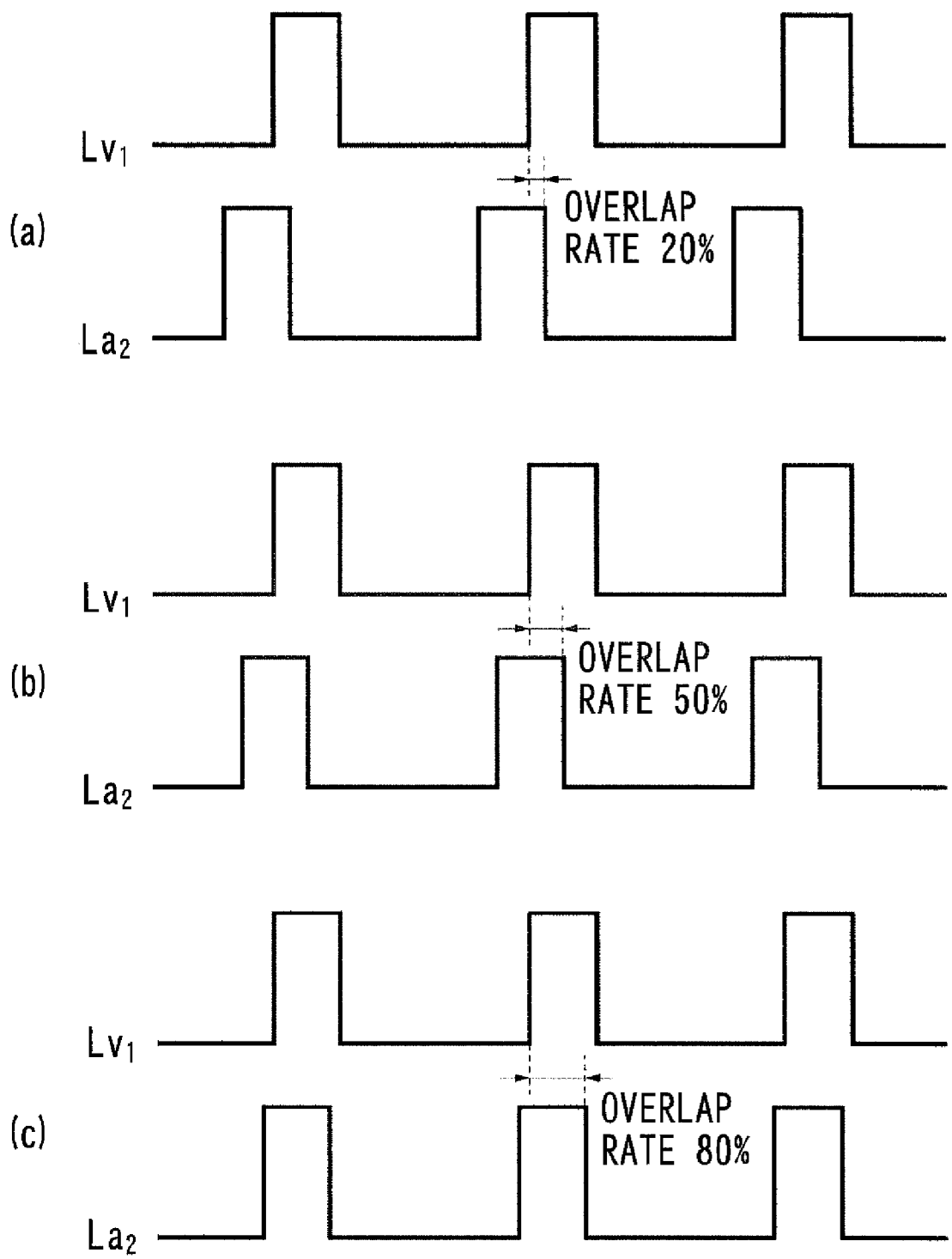

If, on the other hand, the output command input to the control unit 8 via an operation panel or the like is an OFF command for turning off the light output $Lv_2$, the light source controller 83 outputs an output OFF command signal to the light source driver 81. In this case, the light source driver 81 controls the output timing with which the seed light $Ls_1$ with the first wavelength is emitted from the first light source 11 and the output timing with which the seed light $Ls_2$ with the second wavelength is emitted from the second light source 12 relative to each other so as to ensure that the pulse train of the first converted light $Lv_1$ and the pulse train of the second amplified light $La_2$ do not temporally overlap each other at the second wavelength conversion optical element 32, as indicated in FIG. 4 and FIG. 5.

In more specific terms, the light source driver 81 generates the first drive signal and the second drive signal with specific timing (with timing whereby one pulse train assumes the ON state while the other train remains in the OFF state) so that the pulse train of the first converted light $Lv_1$ and the pulse train of the second amplified light $La_2$ do not temporally overlap each other at the second wavelength conversion optical element 32.

The seed light $Ls_1$ with the first wavelength emitted from the first light source 11 and the seed light $Ls_2$ with the second wavelength emitted from the second light source 12 are individually amplified by the fiber amplifier 21 and thus respectively become the first amplified light $La_1$ and the second amplified light $La_2$, which then enter the first wavelength conversion optical element 31 in a condensed state. At the first wavelength conversion optical element 31, the first amplified light $La_1$ alone undergoes wavelength conversion to result in generation of the first converted light $Lv_1$ while the second amplified light $La_2$ with a wavelength manifesting the wavelength difference $\Delta\lambda$ relative to the first wavelength $\lambda_1$ is transmitted without undergoing wavelength conversion. The first converted light $Lv_1$ generated at the first wavelength conversion optical element 31, the second amplified light $La_2$ transmitted through the first wavelength conversion optical element 31 and the component of the first amplified light $La_1$ that is transmitted through the first wavelength conversion optical element 31 without undergoing wavelength conversion all enter the second wavelength conversion optical element 32 in a condensed state.

Settings are selected for the second wavelength conversion optical element 32 so that the pulse trains of the first converted light $Lv_1$ and the second amplified light $La_2$ having entered therein do not temporally overlap each other. The second wavelength conversion optical element 32 is set so that the phase matching condition for generating the sum frequency of the first converted light $Lv_1$ and the second amplified light $La_2$ alone is satisfied without satisfying the phase matching condition for generating the sum frequency of the first converted light $Lv_1$ and the first amplified light $La_1$. However, since the pulse trains of the first converted light $Lv_1$ and the second amplified light $La_2$ having entered the second wavelength conversion optical element 32 do not temporally overlap each other, as described above, no sum frequency is generated at the second wavelength conversion optical element 32 and thus a output light (second converted light) $Lv_2$ with the 355 nm wavelength is not generated. As a result, the laser device LS1 does not provide the light output with the 355 nm wavelength.

ON/OFF control is achieved for the light output $Lv_2$ with the 355 nm wavelength through the measures described above by altering the timing of the pulse train generated as the first drive signal used to drive the first light source 11 and the timing of the pulse train generated as the second drive signal used to drive the second light source 12 relative to each other.

The light output $Lv_2$ can be separated from the first amplified light, the second amplified light, the first converted light and the like that have been transmitted through the second wavelength conversion optical element 32 via a dichroic mirror or the like, which reflects light with wavelength shorter than approximately 400 nm and allows light with longer wavelength to be transmitted through, disposed at an output-end area of the wavelength converting unit 3.

Through these measures, it is ensured that no light with wavelength other than that of the light output is output from the laser device LS1.

An embodiment of ON/OFF control for the light output $Lv_2$ output from the laser device LS1 has been explained so far. Namely, ON/OFF control for the light output $Lv_2$ is achieved by switching between a condition in which the pulse train of the first converted light $Lv_1$ and the pulse train of the second amplified light $La_2$ temporally overlap each other at the second wavelength conversion optical element 32 and a condition in which they do not temporally overlap (see FIG. 2 through FIG. 5). The power of the light output $Lv_2$ can also be controlled in the laser device LS1 achieved in the first embodiment. This control is realized by controlling the overlap rate with which the pulse train of the first converted light $Lv_1$ and the pulse train of the second amplified light $La_2$ temporally overlap at the second wavelength conversion optical element 32. The light output power control, too, is executed by driving the first light source 11 and the second light source 12 with the first drive signal used to drive the first light source 11 and the second drive signal used to drive the second light source 12, generated with relative timing such that the degree to which the pulse train of the first converted light $Lv_1$ and the pulse train of the second amplified light $La_2$ temporally overlap each other at the second wavelength conversion optical element 32 can be adjusted.

FIGS. 6(a) through 6(c) illustrate how the overlap rate for the pulse train of the first converted light $Lv_1$ and the pulse train of the second amplified light $La_2$ at the second wavelength conversion optical element 32 is altered by adjusting the timing with which the first drive signal is generated and the timing with which the second drive signal is generated relative to each other. FIG. 6(a) shows the pulse train of the first converted light $Lv_1$ and the pulse train of the second amplified light $La_2$ made to temporally overlap with an overlap rate of 20% at the second wavelength conversion optical element 32, FIG. 6(b) shows the two pulse trains made to overlap with an overlap rate of approximately 50%, and FIG. 6(c) shows the two pulse trains made to overlap with an overlap rate of 80%.

When the overlap rate is at 20%, as shown in FIG. 6(a), the power of the light output $Lv_2$ generated at the second wavelength conversion optical element 32 is 20% of the power of the light output generated with an overlap rate of 100%. Likewise, when the overlap rate is at 50%, as shown in FIG. 6(b), the power of the light output $Lv_2$ is 50% of the power of the light output generated with an overlap rate of 100% and when the overlap rate is at 80%, as shown in FIG. 6(c), the power of the light output $Lv_2$ is 80% of the power of the light output generated with an overlap rate of 100%.

Namely, by altering the overlap rate for the pulse train of the first converted light $Lv_1$ and the pulse train of the second amplified light $La_2$ at the second wavelength conversion optical element 32 through adjustment of the timing with which the first drive signal used to drive the first light source 11 is generated and the timing with which the second drive signal used to drive the second light source 12 is generated relative to each other, the power of the light output $Lv_2$ can be controlled as desired at high speed within the range of 0 to 100%.

The need to switch at least either the first light source 11 or the second light source 12 in the laser light generating unit 1 to the operating state or the non-operating state in order to turn ON/OFF the light output $Lv_2$ is eliminated in the laser device LS1 achieved in the first embodiment. In addition, it is not necessary to alter the signal waveform of at least either the first drive signal used to drive the first light source 11 or the second drive signal used to drive the second light source 12 in order to control the power of the light output $Lv_2$, either. This means that since both the first light source 11 and the second light source 12 can be engaged in operation in a steady state, the first light source 11 and the second light source 12 are able to operate in a stable manner, which, in turn, makes it possible to generate the seed light $Ls_1$ with the first wavelength and the seed light $Ls_2$ with the second wavelength, each achieving a stable oscillation wavelength and a stable pulse waveform.

Furthermore, the seed light $Ls_1$ with the first wavelength and the seed light $Ls_2$ with the second wavelength enter the fiber amplifier 21 in the amplifying unit 2 continuously, and the first amplified light $La_1$ and the second amplified light $La_2$ are individually amplified by the fiber amplifier 21 and output from the amplifying unit 2 in a steady state. Thus, it is not necessary to alter the gain of the fiber amplifier 21 in order to turn ON/OFF the light output $Lv_2$ or to control the power of the light output $Lv_2$, and the first amplified light $La_1$ and the second amplified light $La_2$ can be output in a stable manner by engaging the fiber amplifier 21 in a steady state in a stable operation.

Moreover, in the wavelength converting unit 3, the first amplified light $La_1$ and the second amplified light $La_2$ enter the first wavelength conversion optical element 31 continuously and the first converted light $Lv_1$ is continuously generated at the first wavelength conversion optical element 31, and the first converted light $Lv_1$ generated at the first wavelength conversion optical element 31 and the second amplified light $La_2$ transmitted through the first wavelength conversion optical element 31 continuously enter the second wavelength conversion optical element 32. This means that the first wavelength conversion optical element 31 and the second wavelength conversion optical element 32 remain thermally stable except for the fluctuations attributed to the change in the amount of heat generated in correspondence to the power of the light output at the second wavelength conversion optical element 32. In particular, the thermal condition in the light path extending from the first light source and the second light source through the first wavelength conversion optical element 31 is very stable.

Thus, high speed and stable control of the light output $Lv_2$ is enabled in the laser device LS1 adopting a simple structure achieved by connecting the fiber amplifier 21 in the amplifying unit 2 in series with the first wavelength conversion optical element 31 and the second wavelength conversion optical element 32 in the wavelength converting unit 3, in which the timing of the generation of the first drive signal used to drive the first light source 11 in the laser light generating unit 1 and the timing of the generation of the second drive signal used to drive the second light source 12 in the laser light generating unit 1 are adjusted relative to each other.

Figure 7:
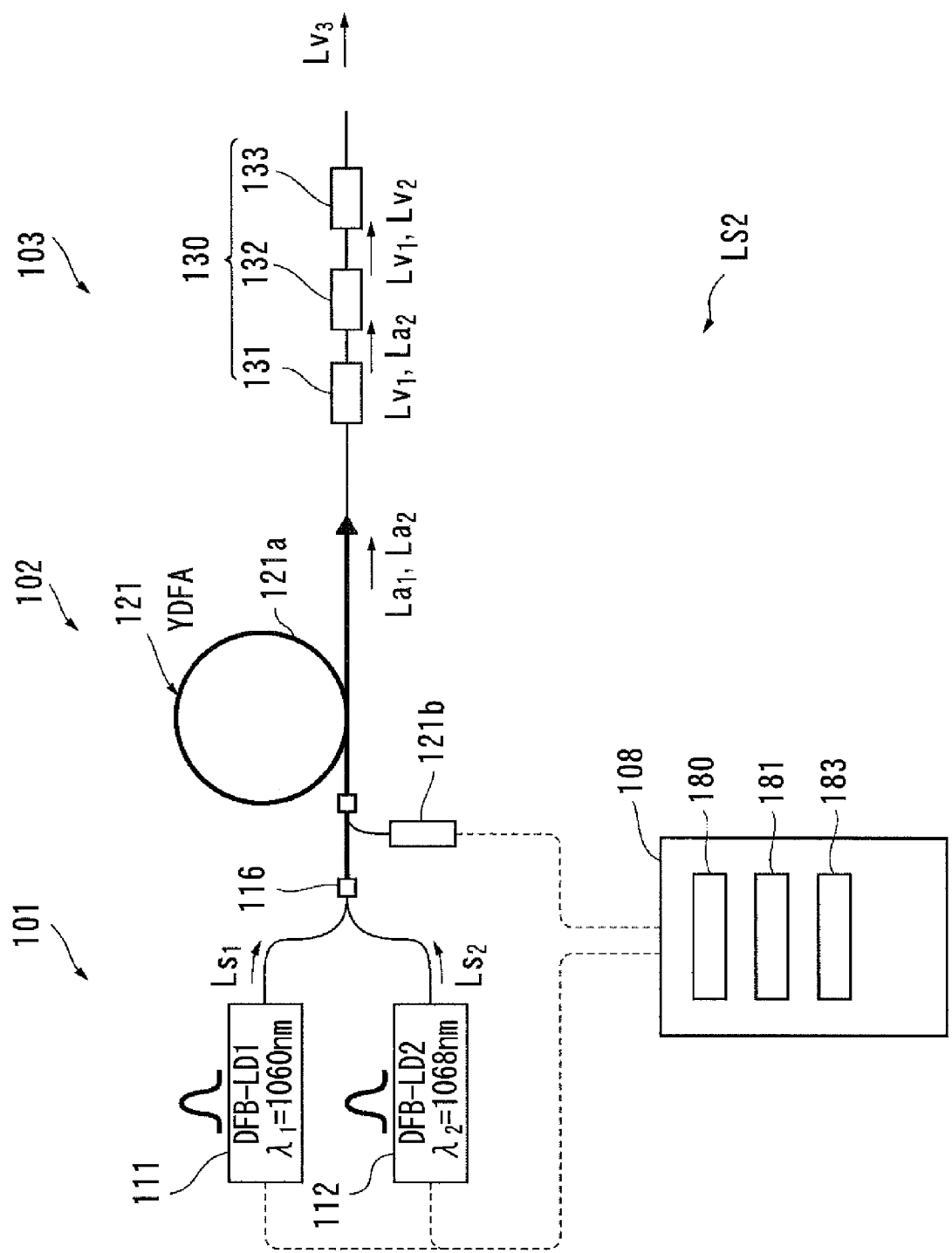

Next, the laser device achieved in the second embodiment of the present invention will be described in reference to FIG. 7. FIG. 7 provides a schematic diagram showing the structure of a laser device LS2 achieved as the second embodiment of the present invention. As does the laser device LS1 in the first embodiment, the laser device LS2 comprises a laser light generating unit 101 that generates pulse laser light (seed light), an amplifying unit 102 that amplifies the seed light generated by the laser light generating unit 1, a wavelength converting unit 103 that converts the wavelength of amplified light output from the amplifying unit 102, and a control unit 108 that controls operations of these units.

In the laser device LS2 achieved in the second embodiment, the seed light generated at the laser light generating unit 101 is infrared light with a wavelength around 1.06 μm and the light output by the wavelength converting unit 103 is ultraviolet light with a wavelength of 266 nm.

The laser light generating unit 101 includes two light sources with oscillation wavelengths thereof slightly different from each other. Namely, the laser light generating unit 101 includes a first light source 111 that generates seed light with a first wavelength $\lambda_1$ and a second light source 112 that generates seed light with a second wavelength $\lambda_2$. A wavelength difference $\Delta\lambda$ between the first wavelength $\lambda_1$ and the second wavelength $\lambda_2$ is 8 nm, the first wavelength $\lambda_1$ is equal to 1060 nm and the second wavelength $\lambda_2$ is equal to 1068 nm.

The first light source 111 and the second light source 112 are each constituted with a DFB (distributed feedback) semiconductor laser. In the laser device LS2 in the second embodiment, repetitive pulse oscillation is induced at a predetermined frequency selected from a frequency range of, for instance, approximately 1 to 10 MHz at the first light source 111 and the second light source 112. The operations of the first light source 111 and the second light source 112 are controlled by the control unit 108. Pulse seed light $Ls_1$ with the first wavelength $\lambda_1$ and pulse seed light $Ls_2$ with the second wavelength $\lambda_2$ output from the laser light generating unit 1 are multiplexed by a coupler 116 and thus enter the amplifying unit 102 in a multiplexed state.

The amplifying unit 102 assumes a structure that includes a fiber amplifier 121 that amplifies the seed light output from the laser light generating unit 101. The fiber amplifier 121 achieves gain in light within a wavelength range that includes the first wavelength $\lambda_1$ and the second wavelength range $\lambda_2$. An ytterbium doped fiber amplifier (YDFA) is preferably used as this fiber amplifier.

An ytterbium doped fiber amplifier (YDFA) 121 is constituted with, as primary components thereof, an amplification fiber 121a having ytterbium (Yb) doped in a core thereof and an excitation light source 121b that provides excitation light to the amplification fiber. The gain at the fiber amplifier 121 is controlled by adjusting the power of the excitation light that excites the amplification fiber 121a, and more specifically, by adjusting, via the control unit 108, the drive power of the excitation light source 121b.

The YDFA 121 amplifies both the seed light $Ls_1$ with the first wavelength $\lambda_1$ of 1060 nm and the seed light $Ls_2$ with the second wavelength $\lambda_2$ of 1068 nm. While the seed light $Ls_1$ with the first wavelength $\lambda_1$ and the seed light $Ls_2$ with the second wavelength $\lambda_2$ are multiplexed via the coupler 116 and thus enter the fiber amplifier 121 in a multiplexed state, they are amplified independently of each other due to the wavelength difference $\Delta\lambda$ of approximately 8 nm between the first wavelength $\lambda_1$ and the second wavelength $\lambda_2$ and thus, first amplified light $La_1$ resulting from amplification of the seed light $Ls_1$ with the first wavelength and second amplified light $La_2$ resulting from amplification of the seed light $Ls_2$ with the second wavelength are output from the fiber amplifier 121 (amplifying unit 2). The first amplified light $La_1$ and the second amplified light $La_2$ output from the amplifying unit 102 enter the wavelength converting unit 103. It is to be noted that as has been explained in reference to the first embodiment, the amplifying unit may be configured by connecting in series a plurality of amplifiers.

The wavelength converting unit 103 includes a wavelength conversion optical system 130, through which the first amplified light $La_1$ and the second amplified light $La_2$, output from the amplifying unit 102, propagates. The wavelength conversion optical system 130, constituted with a first wavelength conversion optical element 131, a second wavelength conversion optical element 132 and a third wavelength conversion optical element 133 as primary components thereof, includes a lens, a waveplate and the like (not shown). The first amplified light $La_1$ and the second amplified light $La_2$, having entered the wavelength converting unit 103, are condensed via the lens, and thus enters the first wavelength conversion optical element 131 in a condensed state.

The first wavelength conversion optical element 131, constituted of a nonlinear optical crystal, generates a second harmonic (first converted light $Lv_1$) with a wavelength that is ½ of the wavelength $\lambda_1$ of the first amplified light $La_1$ through second harmonic generation. However, the second amplified light $La_2$ with the wavelength $\lambda_2$ is allowed to be transmitted through the first wavelength conversion optical element 131 without undergoing wavelength conversion. An LBO ($LiB_3O_5$) crystal is used as the first wavelength conversion optical element 131, in noncritical phase matching (NCPM) state with its temperature adjusted to a predetermined level (to be referred to as a first phase matching temperature) at which a phase matching condition for generating a second harmonic of the first amplified light $La_1$ is satisfied.

The first converted light $Lv_1$ with a wavelength of 530 nm, having been generated as the second harmonic of the first amplified light $La_1$, at the first wavelength conversion optical element 131, the second amplified light $La_2$ with the 1068 nm wavelength having been transmitted through the first wavelength conversion optical element 131 and the component of the first amplified light $La_1$, having been transmitted through the first wavelength conversion optical element 131 without undergoing wavelength conversion, all enter the second wavelength conversion optical element 132.

The second wavelength conversion optical element 132 constituted of a nonlinear optical crystal, generates a second harmonic (second converted light $Lv_2$) having a wavelength that is ½ of the wavelength $\lambda_2$ of the second amplified light $La_2$ through second harmonic generation. However, it allows the first amplified light $La_1$ with the wavelength $\lambda_1$ and the first converted light $Lv_1$ with the wavelength $\lambda_1/2$ to be transmitted without undergoing wavelength conversion. Namely, at each wavelength conversion optical element in the laser device according to the present invention, i.e., at each of the first wavelength conversion optical element 131 and the second wavelength conversion optical element 132, a phase matching condition for generating a second harmonic of one of amplified light alone is satisfied but a phase matching condition for generating a second harmonic of the other amplified light is not satisfied, due to the wavelength difference $\Delta\lambda$ between the first amplified light $La_1$ and the second amplified light $La_2$. An LBO crystal is used as the second wavelength conversion optical element 132 in the noncritical phase matching (NCPM) state, with its temperature adjusted to a second phase matching temperature, at which the phase matching condition for generating the second harmonic of the second amplified light $La_2$ is satisfied.

No walkoff occurs with regard to the converted light (the first converted light $Lv_1$ and the second converted light $Lv_2$) that is generated, as long as the noncritical phase matching (NCPM) state is sustained. For this reason, efficient wavelength conversion is enabled by assuring a sufficient interaction length at both the first wavelength conversion optical element 131 and the second wavelength conversion optical element 132. Since the beam sections of the first converted light $Lv_1$ and the second converted light $Lv_2$ output therefrom have not become ellipsoid, it is not necessary to dispose a beam-shaping optical element such as a cylindrical lens, via which the beam sections are adjusted to circular shapes and thus, no loss occurs in the amount of light entering the third wavelength conversion optical element 133.

The first wavelength conversion optical element 131, which generates a second harmonic (first converted light $Lv_1$) by converting the wavelength of the first amplified light $La_1$, allows the second amplified light $La_2$ to be transmitted without converting its wavelength. The second wavelength conversion optical element 132, which generates a second harmonic (second converted light $Lv_2$) by converting the wavelength of the second amplified light $La_2$, allows the first amplified light $La_1$ to be transmitted without converting its wavelength. Namely, a phase matching condition for generating a second harmonic of one of amplified light alone is satisfied but a phase matching condition for generating a second harmonic of the other amplified light is not satisfied at each of the first wavelength conversion optical element 131 and the second wavelength conversion optical element 132, due to the wavelength difference $\Delta\lambda$ between the first amplified light $La_1$ and the second amplified light $La_2$.

The use of LBO crystals to constitute the first wavelength conversion optical element 131 and the second wavelength conversion optical element 132 will be described in specific detail. For instance, LBO crystals assuming a length of approximately 20 mm measured along the optical axis may be used. At such a wavelength conversion optical element, the acceptance wavelength to satisfy the phase matching condition is approximately several nm for harmonic generation of light having a wavelength substantially equal to the first wavelength $\lambda_1$ at predetermined temperature. Thus, if the temperature of the crystal constituting the first wavelength conversion optical element 131 is set so as to satisfy the phase matching condition for the second harmonic generation of the first amplified light $La_1$, it can be ensured that the phase matching condition for second harmonic generation will not be satisfied with respect to the second amplified light $La_2$ having a wavelength different from that of the first amplified light $La_1$ by 8 nm. A similar rationale applies to the second wavelength conversion optical element 132, as well.

As a result, at the first wavelength conversion optical element 131, the first converted light $Lv_1$ with the 530 nm wavelength is generated in the form of the second harmonic of the first amplified light $La_1$ but the second amplified light $La_2$ is transmitted through the first wavelength conversion optical element 131 with no second harmonic thereof generated. In addition, at the second wavelength conversion optical element 132, the second converted light $Lv_2$ with the 534 nm wavelength is generated in the form of the second harmonic of the second amplified light $La_2$ but the first amplified light $La_1$ and the first converted light $Lv_1$ are transmitted through the second wavelength conversion optical element 132 with no second harmonics thereof generated.

While the first wavelength conversion optical element 131 and the second wavelength conversion element 132 are each constituted with an LBO crystal in the noncritical phase matching state in the example described above, a similar effect attributable to the wavelength difference $\Delta\lambda$ can be induced at a wavelength conversion optical element constituted of a nonlinear optical crystal, such as an LBO crystal or a BBO ($\beta$-$BaB_2O_4$), assuming a critical phase matching (CPM) state. For instance, by setting the angular position of the first wavelength conversion optical element 131 so as to satisfy the phase matching condition for second harmonic generation with regard to the first amplified light $La_1$, it can be ensured that the first amplified light $La_1$ alone undergoes wavelength conversion to result in generation of first converted light $Lv_1$ while allowing the second amplified light $La_2$ to be transmitted without undergoing wavelength conversion. A similar effect can be induced in conjunction with a quasi-phase matching (QPM) crystal such as a PPLN (periodically poled $LiNbO_3$) crystal or a PPLT (periodically poled $LiTaO_3$) crystal.

The first converted light $Lv_1$ with the 530 nm wavelength having been generated at the first wavelength conversion optical element 31 and then transmitted through the second wavelength conversion optical element 132 and the second converted light $Lv_2$ with the 534 nm wavelength having been generated at the second wavelength conversion optical element 132 enter the third wavelength conversion optical element 133 in a condensed state.

The third wavelength conversion optical element 133, constituted of a nonlinear optical crystal, generates the sum frequency of the first converted light $Lv_1$ and the second converted light $Lv_2$ through sum frequency generation. The first converted light $Lv_1$ and the second converted light $Lv_2$ entering the third wavelength conversion optical element 133 may temporally overlap or may not temporally overlap. In either case, a phase matching condition for generating the sum frequency of the first converted light $Lv_1$ and the second converted light $Lv_2$ is satisfied but any of phase matching conditions for generating sum frequencies of the first converted light $Lv_1$ and the first amplified light $La_1$, of the first converted light $Lv_1$ and the second amplified light $La_2$, of the second converted light $Lv_2$ and the first amplified light $La_1$, of the second converted light $Lv_2$ and the second amplified light $La_2$, and of the first amplified light $La_1$ and the second amplified light $La_2$ are not satisfied at the third wavelength conversion optical element 133. Settings are also selected so that none of phase matching conditions for generating second harmonics of these lights are satisfied.

The third wavelength conversion optical element 133 may be constituted of a CLBO ($CsLiB_6O_{10}$) crystal and assume a structure allowing it to be engaged in operation in a type I critical phase matching (CPM) state, which is achieved by adjusting its angular position to a predetermined angular position (phase matching angle) satisfying the phase matching condition for generating the sum frequency of the first converted light $Lv_1$ and the second converted light $Lv_2$. The CLBO crystal, constituting such a third wavelength conversion optical element 133, is processed so that a phase matching condition is satisfied for generating third converted light $Lv_3$ with a wavelength of 266 nm through sum frequency generation of the first converted light $Lv_1$ with the 530 nm wavelength and the second converted light $Lv_2$ with the 534 nm wavelength.

For instance, a CLBO crystal assuming a length of approximately 10 mm measured along the optical axis may be used to constitute the third wavelength conversion element 133. Under such circumstances, the acceptance wavelength range to satisfy the phase matching condition for sum frequency generation is approximately 0.2 nm. Thus, while the phase matching condition for generating the sum frequency of the first converted light $Lv_1$ and the second converted light $Lv_2$ is satisfied to result in generation of the sum frequency, i.e., the third converted light $Lv_3$ with the 266 nm wavelength, none of the phase matching conditions for generating other sum frequencies are satisfied. The third converted light $Lv_3$ with the 266 nm wavelength generated at the third wavelength conversion optical element 133 is emitted from the wavelength converting unit 3 and is ultimately output as light output from the laser device LS.

In the laser device LS2, high speed and stable control of the light output, i.e., the third converted light $Lv_3$ is enabled through control of the operation of the laser light generating unit 101 executed by the control unit 108. As has already been described, the first light source 111, which generates the seed light $Ls_1$ with the first wavelength and the second light source 112, which generates the seed light $Ls_2$ with the second wavelength $\lambda_2$, are disposed in the laser light generating unit 101. In the second embodiment, the control unit 108 controls the operations of the first light source and the second light source so as to achieve high speed and stable control of the light output.

The control unit 108 fulfills basic functions similar to those of the control unit 8 in the first embodiment. Namely, it is configured so as to include a clock generator 180 that generates a clock signal with a frequency of approximately 100 MHz, to be used for reference in control of the operations of the individual units, a light source driver 181 and a light source controller 183. The light source driver 181 generates a first drive signal used to drive the first light source 111 and a second drive signal used to drive the second light source 112 in reference to the clock signal generated by the clock generator 180. The light source controller 183 outputs a command signal to the light source driver 181 based upon an output command input thereto through a processing program in the system in which the laser device LS2 is installed or via an operation panel.

The first drive signal used to drive the first light source 111 and the second drive signal used to drive the second light source 112 in the laser device LS2 achieved in the second embodiment are each generated as a pulse train formed with pulses with a ON time of 1 to several nsec occurring with a pulse repetition frequency of approximately 1 to 10 MHz. The following description will be given by assuming that the first drive signal and the second drive signal are each generated as a pulse train with a 1 nsec ON time and a 1 MHz repetition frequency.

Figure 8:
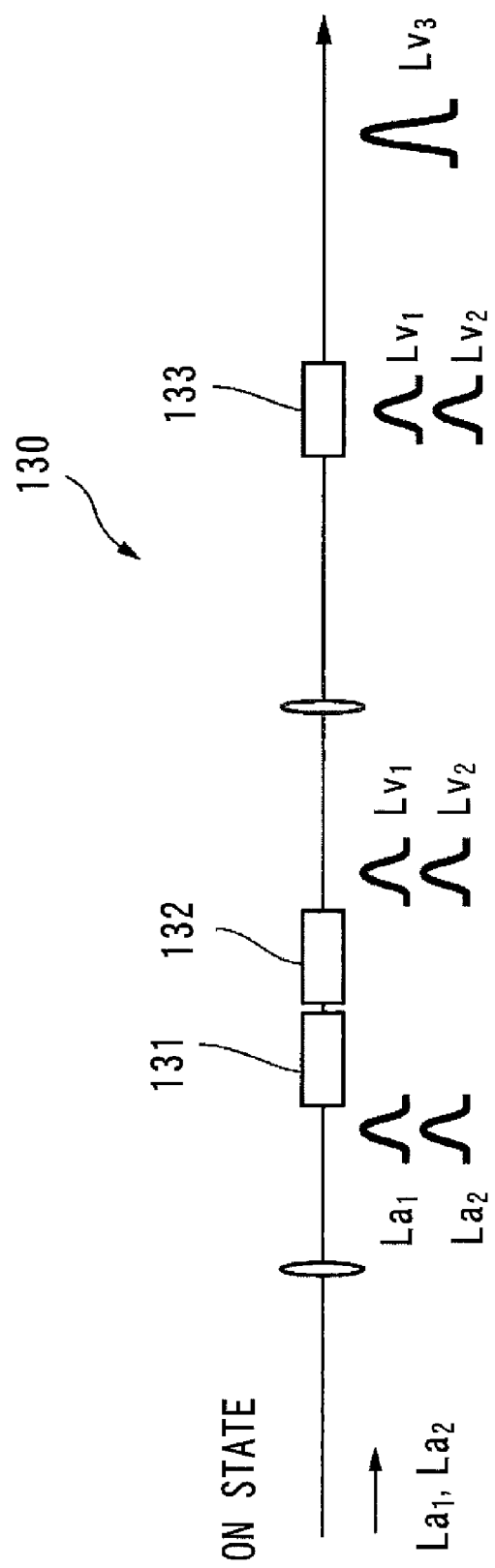
Figure 9:
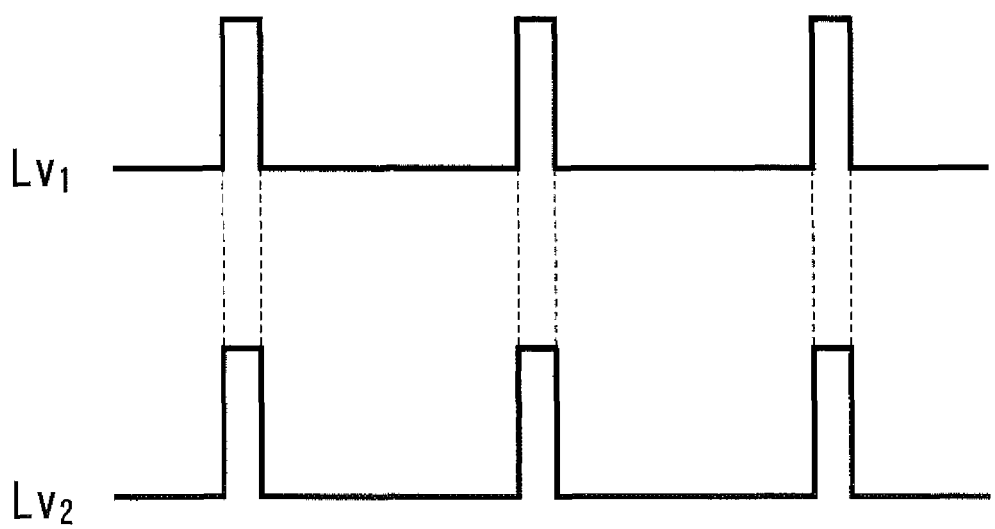

If the output command input to the control unit 108 via an operation panel or the like is an ON command for outputting the third converted light (hereafter referred to as "light output") $Lv_3$ with the 266 nm wavelength, the light source controller 183 outputs an output ON command signal to the light source driver 181. Under these circumstances, the light source driver 181 controls the output timing with which the seed light $Ls_1$ with the first wavelength is emitted from the first light source 111 and the output timing with which the seed light $Ls_2$ with the second wavelength is emitted from the second light source 112 relative to each other so as to achieve a temporal overlap of a pulse train of the first converted light $Lv_1$ and a pulse train of the second converted light $Lv_2$ at the third wavelength conversion optical element 133, as indicated in FIG. 8 and FIG. 9.

In more specific terms, the light source driver 181 generates the first drive signal and the second drive signal with specific timing (identical timing if the first converted light $Lv_1$ and the second converted light $Lv_2$ assume a matching optical path length) so that the pulse train of the first converted light $Lv_1$ and the pulse train of the second converted light $Lv_2$ temporally overlap each other at the third wavelength conversion optical element 133.

The seed light $Ls_1$ with the first wavelength emitted from the first light source 111 and the seed light $Ls_2$ with the second wavelength emitted from the second light source 112 are individually amplified by the fiber amplifier 121 and thus respectively become the first amplified light $La_1$ and the second amplified light $La_2$, which then enter the first wavelength conversion optical element 131 in a condensed state. At the first wavelength conversion optical element 131, the first amplified light $La_1$ alone undergoes wavelength conversion to result in generation of the first converted light $Lv_1$ while the second amplified light $La_2$ with a wavelength manifesting the wavelength difference $\Delta\lambda$ relative to the first wavelength $\lambda_1$ is transmitted through without undergoing wavelength conversion. The first converted light $Lv_1$ generated at the first wavelength conversion optical element 131 and the component of the second amplified light $La_2$ transmitted through the first wavelength conversion optical element 131 both enter the second wavelength conversion optical element 132.

At the second wavelength conversion optical element 132, the second amplified light $La_2$ alone undergoes wavelength conversion to result in generation of the second converted light $Lv_2$. The second converted light $Lv_2$ having been generated at the second wavelength conversion optical element 132 and the first converted light $Lv_1$ having been transmitted through the wavelength conversion optical element 32 enter the third wavelength conversion optical element 133 in a condensed state.

Settings are selected for the third wavelength conversion optical element 133 so that the pulse trains of the first converted light $Lv_1$ and the second converted light $Lv_2$ having entered therein temporally overlap each other. In addition, the third wavelength conversion optical element 133 is set so that the phase matching condition for generating the sum frequency of the first converted light $Lv_1$ and the second converted light $Lv_2$ alone is satisfied without satisfying any of the phase matching conditions for generating other sum frequencies and higher harmonics. As a result, light output (third converted light) $Lv_3$ with the 266 nm wavelength is generated at the third wavelength conversion optical element 133 through the sum frequency generation of the first converted light $Lv_1$ and the second converted light $Lv_2$ and this light is ultimately output from the laser device LS2.

Figure 10:
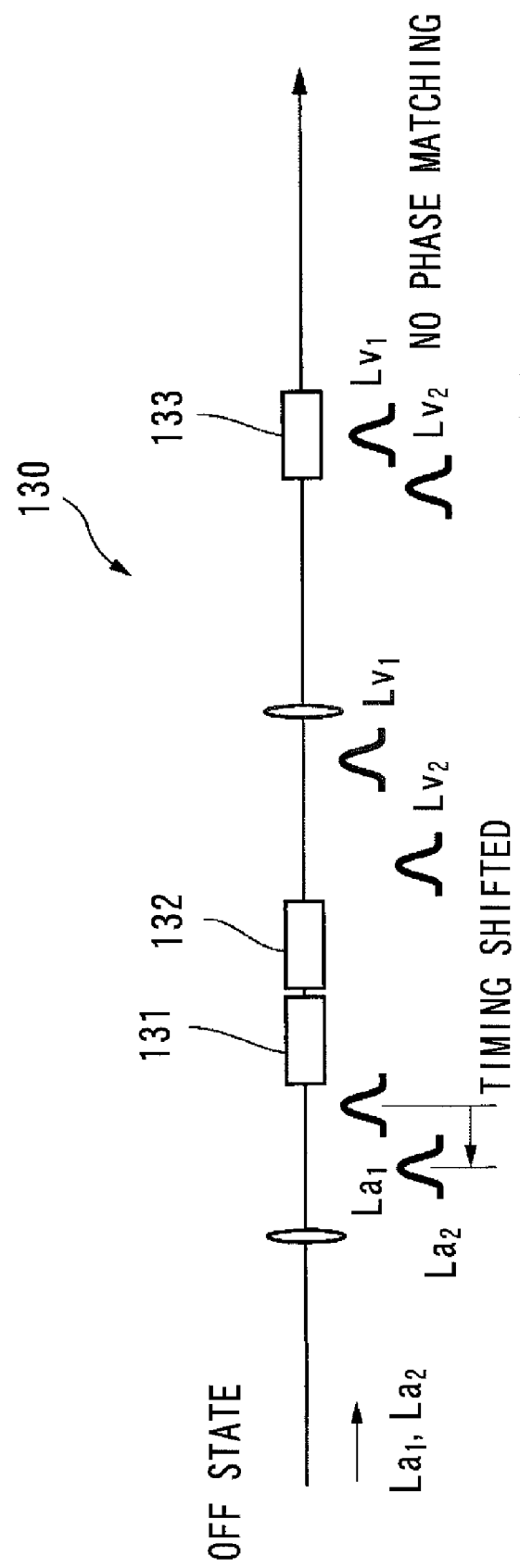
Figure 11:
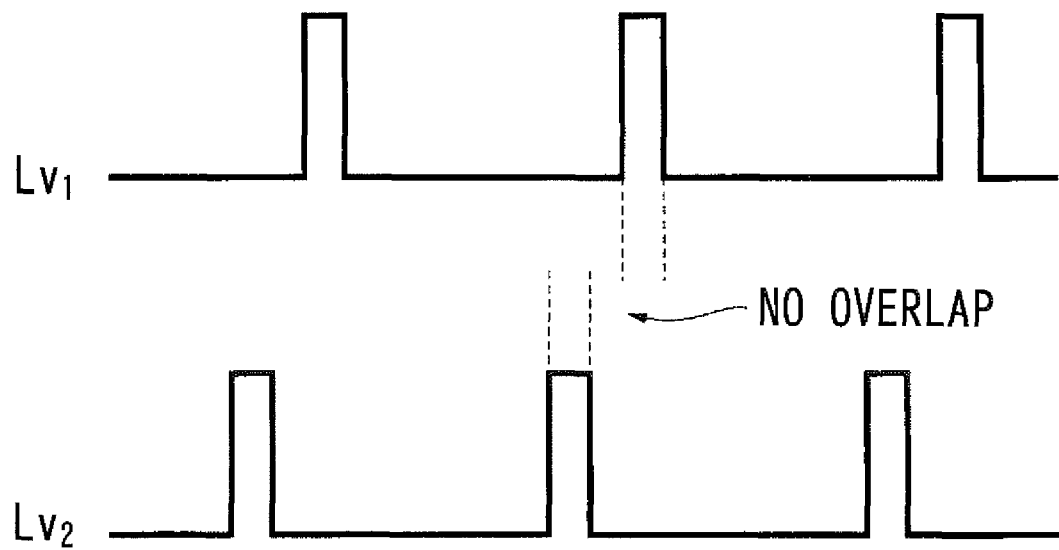
Figure 12:
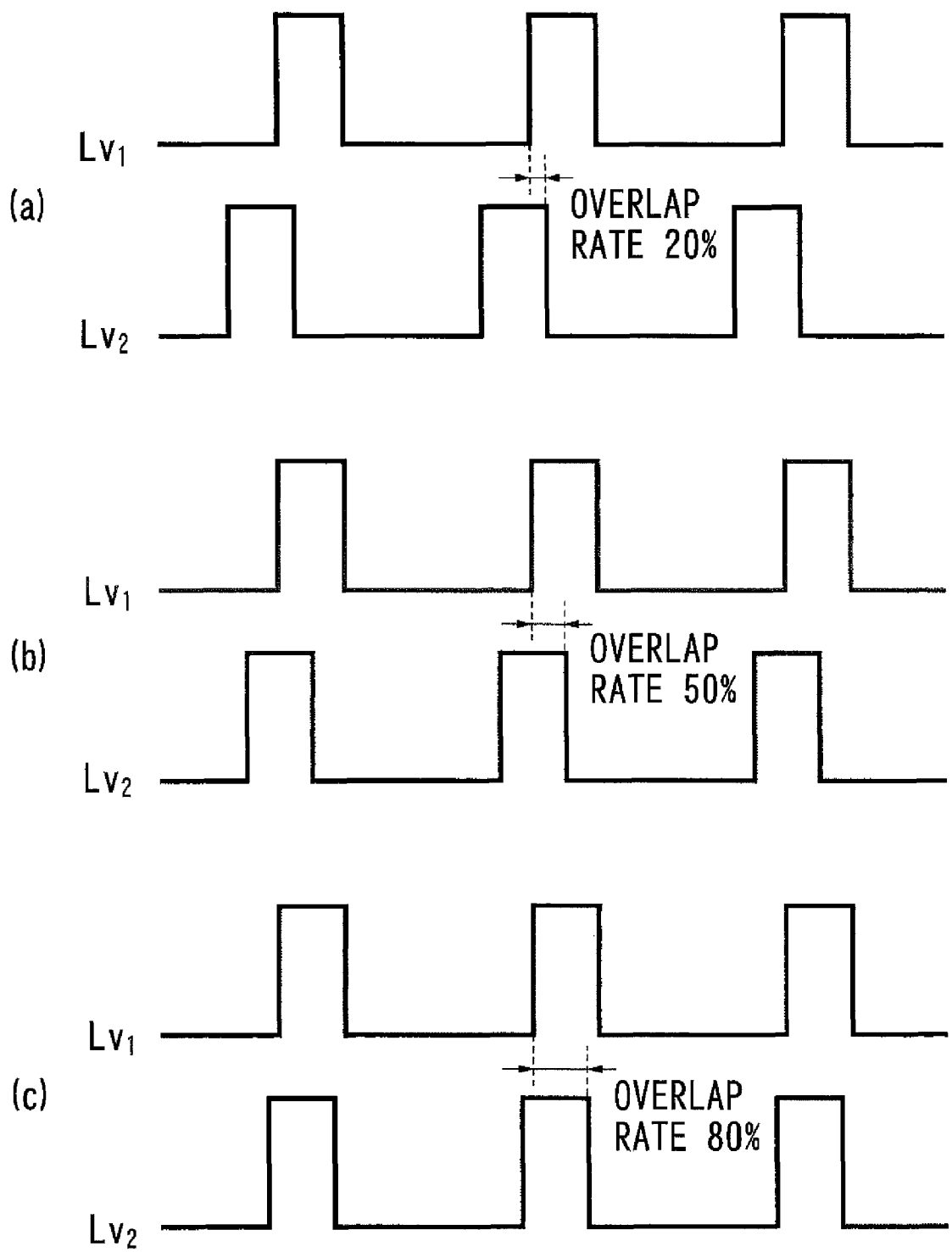

If, on the other hand, the output command input to the control unit 108 via an operation panel or the like is an OFF command for turning off the light output $Lv_3$, the light source controller 183 outputs an output OFF command signal to the light source driver 181. In this case, the light source driver 181 controls the output timing with which the seed light $Ls_1$ with the first wavelength is emitted from the first light source 111 and the output timing with which the seed light $Ls_2$ with the second wavelength is emitted from the second light source 112 relative to each other so as to ensure that the pulse train of the first converted light $Lv_1$ and the pulse train of the second converted light $Lv_2$ do not temporally overlap each other at the third wavelength conversion optical element 133, as indicated in FIG. 10 and FIG. 11.

In more specific terms, the light source driver 181 generates the first drive signal and the second drive signal with specific timing (with timing whereby one pulse train assumes the ON state while the other train remains in the OFF state) so that the pulse train of the first converted light $Lv_1$ and the pulse train of the second converted light $Lv_2$ do not temporally overlap each other at the third wavelength conversion optical element 133.

The seed light $Ls_1$ with the first wavelength emitted from the first light source 111 and the seed light $Ls_2$ with the second wavelength emitted from the second light source 112 are individually amplified by the fiber amplifier 121 and thus respectively become the first amplified light $La_1$ and the second amplified light $La_2$, which then enter the first wavelength conversion optical element 131 in a condensed state. At the first wavelength conversion optical element 131, the first amplified light $La_1$ alone undergoes wavelength conversion to result in generation of the first converted light $Lv_1$ while the second amplified light $La_2$ with a wavelength manifesting the wavelength difference $\Delta\lambda$ relative to the first wavelength $\lambda_1$ is transmitted through without undergoing wavelength conversion. The first converted light $Lv_1$ having been generated at the first wavelength conversion optical element 131 and the component of the second amplified light $La_2$ having been transmitted through the first wavelength conversion optical element 131 both enter the second wavelength conversion optical element 132.

At the second wavelength conversion optical element 132, the second amplified light $La_2$ alone undergoes wavelength conversion to result in generation of the second converted light $Lv_2$. The second converted light $Lv_2$ having been generated at the second wavelength conversion optical element 132 and the first converted light $Lv_1$ having been transmitted through the wavelength conversion optical element 132 enter the third wavelength conversion optical element 133 in a condensed state.

Settings are selected for the third wavelength conversion optical element 133 so that the pulse trains of the first converted light $Lv_1$ and the second converted light $Lv_2$ having entered therein do not temporally overlap each other. In addition, while the phase matching condition for generating the sum frequency of the first converted light $Lv_1$ and the second converted light $Lv_2$ is satisfied, any of the phase matching conditions for generating other sum frequencies and higher harmonics is not satisfied at the third wavelength conversion optical element 133. As a result, a light output $Lv_3$ with the 266 nm wavelength is not generated at the third wavelength conversion optical element 133 and thus the laser device LS2 does not output the light $Lv_3$.

ON/OFF control is achieved for the light output $Lv_3$ with the 266 nm wavelength through the measures described above by altering the timing of the pulse train generated as the first drive signal used to drive the first light source 111 and the timing of the pulse train generated as the second drive signal used to drive the second light source 112 relative to each other.

The light output $Lv_3$ can be separated from the first amplified light, the second amplified light, the first converted light, the second converted light and the like that have been transmitted through the third wavelength conversion optical element 133 via a dichroic mirror or the like, which reflects light with wavelength shorter than approximately 300 nm and allows light with longer wavelength to be transmitted through, disposed at an output-end area of the wavelength converting unit 103. Through these measures, it is ensured that no light with wavelength other than that of the light output is output from the laser device LS2.

An embodiment of ON/OFF control for the light output $Lv_3$ output from the laser device LS2 has been explained so far. Namely, ON/OFF control for the light output $Lv_3$ is achieved by switching between a condition in which the pulse train of the first converted light $Lv_1$ and the pulse train of the second converted light $Lv_2$ temporally overlap each other at the third wavelength conversion optical element 133 and a condition in which they do not temporally overlap (see FIG. 8 through FIG. 11). The power of the light output $Lv_3$ can also be controlled in the laser device LS2 achieved in the second embodiment. This control is realized by controlling the overlap rate with which the pulse train of the first converted light $Lv_1$ and the pulse train of the second converted light $Lv_2$ temporally overlap at the third wavelength conversion optical element 133. The light output power control, too, is executed by driving the first light source 111 and the second light source 112 with the first drive signal used to drive the first light source 111 and the second drive signal used to drive the second light source 112, generated with relative timing such that the degree to which the pulse train of the first converted light $Lv_1$ and the pulse train of the second converted light $Lv_2$ temporally overlap each other at the third wavelength conversion optical element 133 can be adjusted.

FIGS. 12(a) through 12(c) illustrate how the overlap rate for the pulse train of the first converted light $Lv_1$ and the pulse train of the second converted light $Lv_2$ at the third wavelength conversion optical element 133 is altered by adjusting the timing with which the first drive signal is generated and the timing with which the second drive signal is generated relative to each other. FIG. 12(a) shows the pulse train of the first converted light $Lv_1$ and the pulse train of the second converted light $Lv_2$ made to temporally overlap with an overlap rate of 20% at the third wavelength conversion optical element 133, FIG. 12(b) shows the two pulse trains made to overlap with an overlap rate of approximately 50%, and FIG. 12(c) shows the two pulse trains made to overlap with an overlap rate of 80%.

When the overlap rate is at 20%, as shown in FIG. 12(a), the power of the light output $Lv_3$ generated at the third wavelength conversion optical element 133 is 20% of the power of the light output generated with an overlap rate of 100%. Likewise, when the overlap rate is at 50%, as shown in FIG. 12(b), the power of the light output $Lv_3$ is 50% of the power of the light output generated with an overlap rate of 100% and when the overlap rate is at 80%, as shown in FIG. 12(c), the power of the light output $Lv_3$ is 80% of the power of the light output generated with an overlap rate of 100%.

Namely, by altering the overlap rate for the pulse train of the first converted light $Lv_1$ and the pulse train of the second converted light $Lv_2$ at the third wavelength conversion optical element 133 through adjustment of the timing with which the first drive signal used to drive the first light source 111 is generated and the timing with which the second drive signal used to drive the second light source 112 is generated relative to each other, the power of the light output $Lv_2$ can be controlled as desired at high speed within the range of 0 to 100%.

The need to switch at least either the first light source 111 or the second light source 112 in the laser light generating unit 101 to the operating state or the non-operating state in order to turn ON/OFF the light output $Lv_3$ is eliminated in the laser device LS2 achieved in the second embodiment. In addition, it is not necessary to alter the signal waveform of at least either the first drive signal used to drive the first light source 111 or the second drive signal used to drive the second light source 112 in order to control the power of the light output $Lv_2$, either. This means that since both the first light source 111 and the second light source 112 can be engaged in operation in a steady state, the first light source 111 and the second light source 112 are able to operate in a stable manner, which, in turn, makes it possible to generate the seed light $Ls_1$ with the first wavelength and the seed light $Ls_2$ with the second wavelength, each achieving a stable oscillation wavelength and a stable pulse waveform.

Furthermore, the seed light $Ls_1$ with the first wavelength and the seed light $Ls_2$ with the second wavelength continuously enter the fiber amplifier 121 in the amplifying unit 102, and the first amplified light $La_1$ and the second amplified light $La_2$ are individually amplified by the fiber amplifier 121, and are output steadily from the amplifying unit 102 in a steady state. Thus, it is not necessary to alter the gain of the fiber amplifier 121 in order to turn ON/OFF the light output $Lv_3$ or to control the power of the light output $Lv_3$, and the first amplified light $La_1$ and the second amplified light $La_2$ can be output in a stable manner by engaging the fiber amplifier 121 in a steady state in a stable operation.

Moreover, in the wavelength converting unit 103, the first amplified light $La_1$ and the second amplified light $La_2$ enter the first wavelength conversion optical element 131 continuously and the first converted light $Lv_1$ is continuously generated at the first wavelength conversion optical element 131, and the first converted light $Lv_1$ and the second amplified light $La_2$ continuously enter the second wavelength conversion optical element 132 where the second converted light $Lv_2$ is continuously generated. In addition, the first converted light $Lv_1$ and the second converted light $Lv_2$ continuously enter the third wavelength conversion optical element. The first through third wavelength conversion optical elements 131 through 133 are thermally stable and, in particular, the thermal condition in the light path extending to the second wavelength conversion element is very stable.

Thus, high speed and stable control of the light output Lv3 is enabled in the laser device LS2 adopting a simple structure achieved by connecting the fiber amplifier 121 in the amplifying unit 102 in series with the first through third wavelength conversion optical elements 131 through 133 in the wavelength converting unit 103, in which the timing of the generation of the first drive signal used to drive the first light source 111 and the timing of the generation of the second drive signal used to drive the second light source 112 in the laser light generating unit 101 are adjusted relative to each other.

In each of the structural examples described above, pulse oscillation is induced at the first light source and the second light source and the output condition of the light output (the second converted light output from the LS1, the third converted light output from the LS2) is controlled by altering the timing with which the drive signal for the first light source is generated and the timing with which the drive signal for the second light source is generated relative to each other. However, the present invention is not limited to such a structural mode and may be adopted in any other structure, as long as the output timing with which the seed light $Ls_1$ with the first wavelength is output from the laser light generating unit and the output timing with which the seed light $Ls_2$ with the second wavelength is output from the laser light generating unit can be controlled at high speed.

For instance, an external modulator such as an electro-optic modulator (EOM) may be disposed at an emission end area of at least either the first light source or the second light source so as to output the seed light $Ls_1$ with the first wavelength and/or the seed light $Ls_2$ with the second wavelength from the laser light generating unit by extracting, via the external modulator, part of laser light generated through CW oscillation or pulse oscillation with predetermined timing. A laser device adopting this embodiment is capable of outputting a light output with a pulse waveform manifesting steeper rise and fall.

It is to be noted that while the wavelength difference $\Delta\lambda$ between the first wavelength $\lambda_1$ and the second wavelength $\lambda_2$ is 10 nm and 8 nm respectively in the structures achieved in the first embodiment and the second embodiment described above, an optimal value can be set for the wavelength difference $\Delta\lambda$ in correspondence to specific structural details of the amplifying unit 2 and the wavelength converting unit. It is also to be noted that besides the structures described in reference to the embodiments, as an alternative way of achieving a phase matching condition under which a second harmonic of the first amplified light $La_1$ alone may be generated at the first wavelength conversion optical element, another structure may be adopted where the first amplified light $La_1$ and the second amplified light $La_2$ enter the first wavelength conversion optical element with their planes of polarization set perpendicular to each other. If the second wavelength conversion optical element is used in the type I phase matching condition in conjunction with this positional arrangement, there will be no need to install a dual wavelength waveplate between the first wavelength conversion optical element and the second wavelength conversion optical element.

In addition, in both the first embodiment and the second embodiment described above, seed light with two wavelengths around 1.06 μm is output from the laser light generating unit 1 and is propagated through the plurality of wavelength conversion optical elements in the wavelength converting unit so as to output a light output with the 355 nm wavelength or the 266 nm wavelength, resulting from wavelength conversion. However, the present invention is not limited to these examples and optimal values should be selected as required with regard to the wavelength range for the seed light, the number of wavelength conversion optical elements, the positional arrangement of the wavelength conversion optical elements, the wavelength of the light output and the like.

The laser device according to the present invention as described above is a compact, lightweight unit assuming easy handling, and may be adopted in an ideal manner in systems such as optical processing devices including exposure devices and laser beam forming devices, inspection devices used to inspect photomasks and wafers, observation devices including microscopes, telescopes and the like, measurement devices including length measuring devices, profile measuring devices and the like, and laser treatment devices.

Figure 13:
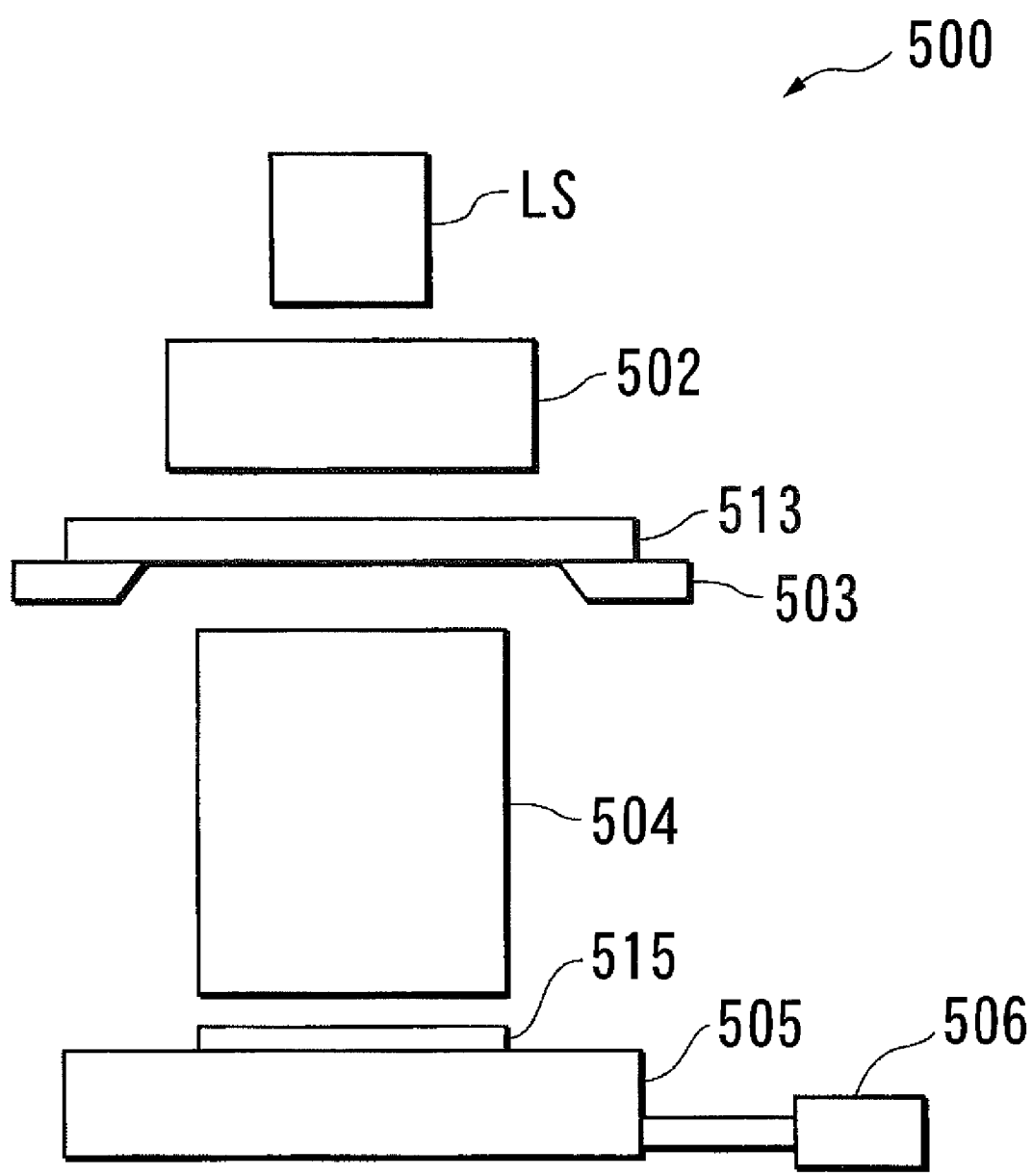

An exposure device used in a photolithography process in semiconductor production or liquid crystal panel production embodying a system equipped with the laser device according to the present invention as a first application example will be described in reference to FIG. 13 schematically showing its structure. An exposure device 500 transfers a precise, minute device pattern, drawn on a silica glass photomask 513, onto an exposure target object 515, such as a semiconductor wafer or a glass substrate with a photoresist coated thereon, by optically projecting the device pattern.

The exposure device 500 comprises the laser device LS according to the present invention, an illumination optical system 502, a mask support stage 503 that holds the photomask 513, a projection optical system 504, an exposure target object support table 505 that holds the exposure target object 515, and a drive mechanism 506 that displaces the exposure target object support table 505 within a horizontal plane. The illumination optical system 502 comprising a plurality of lens groups, illuminates the photomask 513 held on the mask support stage 503 with laser light output from the laser device LS. The projection optical system 504 also comprises a plurality of lens groups, projects light having been transmitted through the photomask 513 onto the exposure target object 515 placed on the exposure target object support table.

In the exposure device 500 structured as described above, the laser light output from the laser device LS enters the illumination optical system 502, and the laser light, adjusted into the form of a specific light flux, then illuminates the photomask 513 held at the mask support stage 503. Light having passed through the photomask 513 with the device pattern formed thereon is illuminated, via the projection optical system 504, onto a predetermined position at the exposure target object 515 held on the exposure target object support table 505. As a result, an image of the device pattern on the photomask 513 is formed on the exposure target object 515, such as a semiconductor wafer or a liquid crystal panel, at a predetermined magnification and the exposure target object 515 is thus exposed in correspondence to the image of the device pattern.

Figure 14:
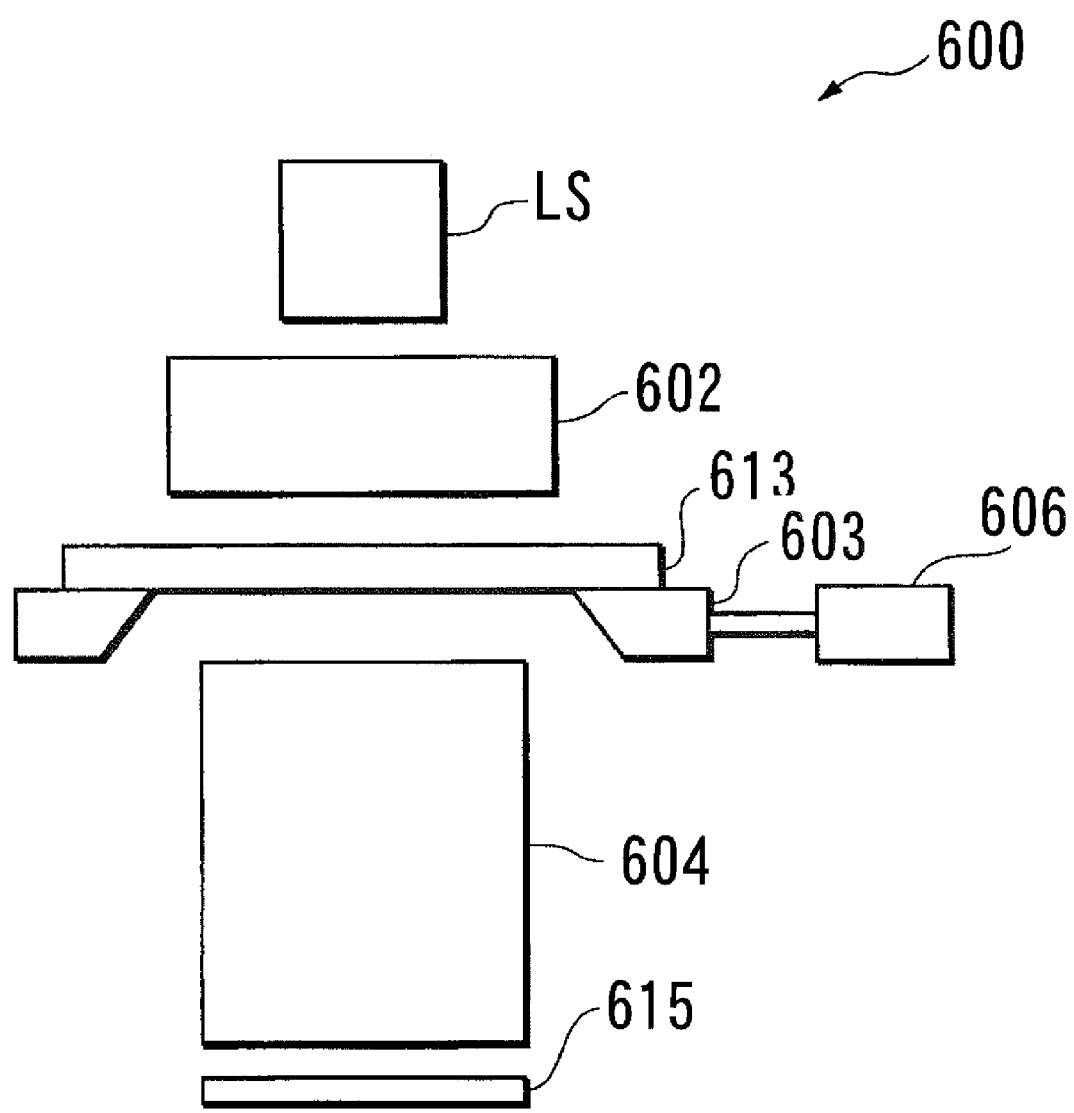

Next, an inspection device used in an inspection process through which a photomask, a liquid crystal panel, a wafer or the like (i.e., an inspection target object) is inspected, embodying a system equipped with the laser device according to the present invention as a second application example, will be described in reference to FIG. 14, schematically showing its structure. An inspection device 600 shown in FIG. 8 is preferably used for applications including inspection of minute device patterns drawn on an inspection target object 613 manifesting transparency such as a photomask.

The inspection device 600 comprises the laser device LS, an illumination optical system 602, an inspection target object support stage 603 that holds the inspection target object 613, a projection optical system 604, a TDI (time delay integration) sensor 615 that detects light departing the inspection target object 613 and a drive mechanism 606 that displaces the inspection target object support stage 603 within a horizontal plane. The illumination optical system 602 comprising a plurality of lens groups illuminates the inspection target object 613 held on the inspection target object support stage 603 with laser light output from the laser device LS. The projection optical system 604 comprises a plurality of lens groups, projects light having been transmitted through the inspection target object 613 onto the TDI sensor 615.

In the inspection device 600 structured as described above, laser light output from the laser device LS enters the illumination optical system 602, and the laser light, adjusted into the form of a specific light flux, then illuminates the inspection target object 613 such as a photomask held at the inspection target object support stage 603. An image such as a device pattern is formed on the inspection target object 613, which may be, for instance, a photomask, and light departing the inspection target object 613 (transmitted light in this example) is projected via the projection optical system 604 onto the TDI sensor 615. During this process, the horizontal displacement of the inspection target object support stage 603 via the drive mechanism 606 and the transfer clock for the signal output from the TDI sensor 615 are synchronously controlled.

In the inspection device structured as described above, the image of the device pattern on the inspection target object 613 is detected by the TDI sensor 615, and any defect in the device pattern formed on the inspection target object is extracted through comparison of the device pattern on the inspection target object 613 thus detected with a reference image. It is to be noted that even when the inspection target object 613 is not a transparency object, such as a wafer, similar functions can still be fulfilled by adopting a structure whereby light reflected at the inspection target object is directed to enter the projection optical system 604 and then is guided to the TDI censor 615.

The structures described above simply represent examples and the present invention is in no way limited to the structural details of the embodiments.

The disclosures of the following priority patent applications are herein incorporated by reference:
Japanese Patent Application No. 2012-169643 filed Jul. 31, 2012
Japanese Patent Application No. 2012-169644 filed Jul. 31, 2012

EXPLANATION OF REFERENCE NUMERALS

LS laser device
1, 101 laser light generating unit
2, 102 amplifying unit
3, 103 wavelength converting unit
8, 108 control unit
11, 111 first light source
12, 112 second light source
21, 121 fiber amplifier (amplifier)
30, 130 wavelength conversion optical system
31, 131 first wavelength conversion optical element
32, 132 second wavelength conversion optical element
500 exposure device
502 illumination optical system
503 mask support stage
504 projection optical system
505 exposure target object support table
513 photomask
515 exposure target object
600 inspection device
602 illumination optical system
603 inspection target object support stage
604 projection optical system
613 inspection target object
615 TDI sensor

The invention claimed is:
1. A laser device, comprising:
a laser light generating unit that includes a first light source that generates pulse laser light with a first wavelength and a second light source that generates pulse laser light with a second wavelength;
an amplifying unit equipped with an amplifier achieving gain in light in a wavelength range that includes the first wavelength and the second wavelength, which outputs first amplified light obtained by amplifying the laser light with the first wavelength and second amplified light obtained by amplifying the laser light with the second wavelength;
a wavelength converting unit that converts light from one wavelength to another wavelength, the wavelength converting unit including a wavelength conversion optical element, which either converts the first amplified light to first converted light through wavelength conversion and generates a light output through wavelength conversion of the first converted light and the second amplified light or converts the first amplified light to first converted light and the second amplified light to second converted light and generates a light output through wavelength conversion of the first converted light and the second converted light; and
a control unit that controls operation of the laser light generating unit, wherein:
the control unit controls an output condition of the light output by adjusting a temporal overlap of the first converted light and the second amplified light or a temporal overlap of the first converted light and the second converted light at a position at which the light output is generated in the wavelength converting unit, through control of timing with which the laser light with the first wavelength is output from the first light source and the timing with which the laser light with the second wavelength is output from the second light source relative to each other; and a wavelength of the light output from the wavelength converting unit is different from the first wavelength and is also different from the second wavelength.

2. The laser device according to claim 1, wherein:

the wavelength converting unit includes a first wavelength conversion optical element that converts the first amplified light to first converted light through wavelength conversion and allows the second amplified light to be transmitted and a second wavelength conversion optical element that generates second converted light through wavelength conversion of the second amplified light transmitted through the first wavelength conversion optical element and the first converted light; and the control unit controls an output condition of the second converted light by adjusting a temporal overlap of the first converted light and the second amplified light at the second wavelength conversion optical element through control of the timing with which the laser light with the first wavelength is output from the first light source and the timing with which the laser light with the second wavelength is output from the second light source relative to each other.

3. The laser device according to claim 2, wherein:

the first wavelength and the second wavelength are individually set to such values that a phase matching condition for generating a sum frequency of the first converted light and the second amplified light is satisfied and a phase matching condition for generating a sum frequency of the first converted light and the first amplified light is not satisfied at the second wavelength conversion optical element.

4. The laser device according to claim 2, wherein:

the first wavelength and the second wavelength are individually set to such values that a phase matching condition for generating a harmonic of the first amplified light is satisfied and a phase matching condition for generating a harmonic of the second amplified light is not satisfied at the first wavelength conversion optical element.

5. The laser device according to claim 2, wherein:

the control unit controls ON/OFF of the second converted light provided as the light output by switching between a condition in which the first converted light and the second amplified light temporally overlap and a condition in which the first converted light and the second amplified light do not temporally overlap at the second wavelength conversion optical element.

6. The laser device according to claim 2, wherein:

the control unit controls power of the second converted light provided as the light output by altering the extent to which the first converted light and the second amplified light temporally overlap at the second wavelength conversion optical element.

7. The laser device according to claim 1, wherein:

the wavelength converting unit includes a first wavelength conversion optical element that converts the first amplified light to first converted light through wavelength conversion and allows the second amplified light to be transmitted, a second wavelength conversion optical element that converts the second amplified light having been transmitted through the first wavelength conversion optical element to second converted light through wavelength conversion and allows the first converted light to be transmitted, and a third wavelength conversion optical element that generates third converted light through wavelength conversion of the first converted light and the second converted light; and the control unit controls an output condition of the third converted light by adjusting a temporal overlap of the first converted light and the second converted light at the third wavelength conversion optical element through control of the timing with which the laser light with the first wavelength is output from the first light source and the timing with which the laser light with the second wavelength is output from the second light source relative to each other.

8. The laser device according to claim 7, wherein:

the first wavelength and the second wavelength are individually set to such values that a phase matching condition for generating a sum frequency of the first converted light and the second converted light is satisfied and any of phase matching conditions for generating sum frequencies and second harmonics other than the sum frequency is not satisfied at the third wavelength conversion optical element.

9. The laser device according to claim 7, wherein:

the first wavelength and the second wavelength are individually set to such values that a phase matching condition for generating a harmonic of the first amplified light is satisfied and a phase matching condition for generating a harmonic of the second amplified light is not satisfied at the first wavelength conversion optical element and that a phase matching condition for generating a harmonic of the second amplified light is satisfied and a phase matching condition for generating a harmonic of the first amplified light is not satisfied at the second wavelength conversion optical element.

10. The laser device according to claim 7, wherein:

the control unit controls ON/OFF of the third converted light provided as the light output by switching between a condition in which the first converted light and the second converted light temporally overlap and a condition in which the first converted light and the second amplified light do not temporally overlap at the third wavelength conversion optical element.

11. The laser device according to claim 7, wherein:

the control unit controls power of the third converted light provided as the light output by altering the extent to which the first converted light and the second converted light temporally overlap at the third wavelength conversion optical element.

12. An exposure device, comprising:

a laser device according to claim 1;

a mask supporting unit that holds a photomask having a predetermined exposure pattern formed thereat;

an exposure target object supporting unit that holds an exposure target object;

an illumination optical system that illuminates the photomask held at the mask supporting unit with laser light output from the laser device; and a projection optical system that projects light having been transmitted through the photomask onto the exposure target object held at the exposure target object supporting unit.

13. An inspection device, comprising:
a laser device according to claim 1,
an inspection target object supporting unit that holds an inspection target object;
an illumination optical system that illuminates the inspection target object held at the inspection target object supporting unit with laser light output from the laser device; and
a projection optical system that projects light departing the inspection target object toward a detector.

14. A laser device, comprising:
a laser light generating unit that includes a first light source that generates pulse laser light with a first wavelength and a second light source that generates pulse laser light with a second wavelength;
an amplifying unit equipped with an amplifier achieving gain in light in a wavelength range that includes the first wavelength and the second wavelength, which outputs first amplified light obtained by amplifying the laser light with the first wavelength and second amplified light obtained by amplifying the laser light with the second wavelength;
a wavelength converting unit that converts light from one wavelength to another wavelength, the wavelength converting unit including a wavelength conversion optical element, which either converts the first amplified light to first converted light through wavelength conversion and generates a light output through wavelength conversion of the first converted light and the second amplified light or converts the first amplified light to first converted light and the second amplified light to second converted light and generates a light output through wavelength conversion of the first converted light and the second converted light; and
a control unit that controls operation of the laser light generating unit, wherein:
the control unit controls an output condition of the light output by adjusting a temporal overlap of the first converted light and the second amplified light or a temporal overlap of the first converted light and the second converted light at a position at which the light output is generated in the wavelength converting unit, through control of timing with which the laser light with the first wavelength is output from the first light source and the timing with which the laser light with the second wavelength is output from the second light source relative to each other;
a wavelength of the light output from the wavelength converting unit is different from the first wavelength and is also different from the second wavelength;
the wavelength converting unit includes a first wavelength conversion optical element that converts the first amplified light to first converted light through wavelength conversion and allows the second amplified light to be transmitted and a second wavelength conversion optical element that generates second converted light through wavelength conversion of the second amplified light transmitted through the first wavelength conversion optical element and the first converted light; and
the control unit controls an output condition of the second converted light by adjusting a temporal overlap of the first converted light and the second amplified light at the second wavelength conversion optical element through control of the timing with which the laser light with the first wavelength is output from the first light source and the timing with which the laser light with the second wavelength is output from the second light source relative to each other.

15. A laser device, comprising:
a laser light generating unit that includes a first light source that generates pulse laser light with a first wavelength and a second light source that generates pulse laser light with a second wavelength;
an amplifying unit equipped with an amplifier achieving gain in light in a wavelength range that includes the first wavelength and the second wavelength, which outputs first amplified light obtained by amplifying the laser light with the first wavelength and second amplified light obtained by amplifying the laser light with the second wavelength;
a wavelength converting unit that converts light from one wavelength to another wavelength, the wavelength converting unit including a wavelength conversion optical element, which either converts the first amplified light to first converted light through wavelength conversion and generates a light output through wavelength conversion of the first converted light and the second amplified light or converts the first amplified light to first converted light and the second amplified light to second converted light and generates a light output through wavelength conversion of the first converted light and the second converted light; and
a control unit that controls operation of the laser light generating unit, wherein:
the control unit controls an output condition of the light output by adjusting a temporal overlap of the first converted light and the second amplified light or a temporal overlap of the first converted light and the second converted light at a position at which the light output is generated in the wavelength converting unit, through control of timing with which the laser light with the first wavelength is output from the first light source and the timing with which the laser light with the second wavelength is output from the second light source relative to each other;
a wavelength of the light output from the wavelength converting unit is different from the first wavelength and is also different from the second wavelength;
the wavelength converting unit includes a first wavelength conversion optical element that converts the first amplified light to first converted light through wavelength conversion and allows the second amplified light to be transmitted, a second wavelength conversion optical element that converts the second amplified light having been transmitted through the first wavelength conversion optical element to second converted light through wavelength conversion and allows the first converted light to be transmitted, and a third wavelength conversion optical element that generates third converted light through wavelength conversion of the first converted light and the second converted light; and
the control unit controls an output condition of the third converted light by adjusting a temporal overlap of the first converted light and the second converted light at the third wavelength conversion optical element through control of the timing with which the laser light with the first wavelength is output from the first light source and the timing with which the laser light with the second wavelength is output from the second light source relative to each other.

* * * * *